(12) United States Patent
Leparmentier et al.

(10) Patent No.: US 12,076,100 B2
(45) Date of Patent: Sep. 3, 2024

(54) ROBOTIC SYSTEMS AND METHODS FOR CONCOMITANT ENDOSCOPIC AND PERCUTANEOUS MEDICAL PROCEDURES

(71) Applicant: Auris Health, Inc., Redwood City, CA (US)

(72) Inventors: Richard August Leparmentier, San Carlos, CA (US); Eric Davidson, Hillsborough, CA (US); Enrique Romo, Dublin, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/586,198

(22) Filed: Sep. 27, 2019

(65) Prior Publication Data

US 2020/0100855 A1 Apr. 2, 2020

Related U.S. Application Data

(60) Provisional application No. 62/738,706, filed on Sep. 28, 2018.

(51) Int. Cl.
*A61B 34/37* (2016.01)
*A61B 1/01* (2006.01)
(Continued)

(52) U.S. Cl.
CPC .............. *A61B 34/37* (2016.02); *A61B 1/01* (2013.01); *A61B 1/3132* (2013.01); *A61B 5/065* (2013.01); *A61B 2034/301* (2016.02)

(58) Field of Classification Search
CPC ......... A61B 34/37; A61B 1/01; A61B 1/3132; A61B 2034/301; A61B 5/065
See application file for complete search history.

(56) References Cited

U.S. PATENT DOCUMENTS

| 4,644,237 A | 2/1987 | Frushour et al. |
| 4,745,908 A | 5/1988 | Wardle |

(Continued)

FOREIGN PATENT DOCUMENTS

| CN | 1364275 | 8/2002 |
| CN | 1511249 | 7/2004 |

(Continued)

OTHER PUBLICATIONS

Blankenstein, Jun. 2008, Dynamic Registration and High Speed Visual Servoing in Robot-Assisted Surgery, Katholieke Universiteit Leuven, Leuven, Belgium.

(Continued)

*Primary Examiner* — Sean A Frith
(74) *Attorney, Agent, or Firm* — Chang & Hale LLP

(57) ABSTRACT

Certain aspects relate to systems and techniques for endoscopically-assisted percutaneous medical procedures. A method can include inserting a first medical instrument having an elongated shaft and a first position sensor into a treatment region of a patient through a natural orifice of the patient. A first position of the first medical instrument within the treatment region can be determined with the first position sensor. A target location can be defined within the treatment region that is distanced from the determined first position. A second medical instrument can be percutaneously guided toward the target location. The method can be performed on a robotically-enabled medical system.

25 Claims, 27 Drawing Sheets

(51) Int. Cl.
*A61B 1/313* (2006.01)
*A61B 5/06* (2006.01)
*A61B 34/30* (2016.01)

(56) References Cited

U.S. PATENT DOCUMENTS

| | | |
|---|---|---|
| 4,748,969 A | 6/1988 | Wardle |
| D307,263 S | 4/1990 | Ishida |
| 5,190,557 A | 3/1993 | Borodulin et al. |
| 5,194,791 A | 3/1993 | Cull |
| 5,199,417 A | 4/1993 | Muller et al. |
| 5,251,611 A | 10/1993 | Zehel et al. |
| 5,273,025 A | 12/1993 | Sakiyam et al. |
| 5,280,781 A | 1/1994 | Oku |
| 5,408,263 A | 4/1995 | Kikuchi |
| 5,526,812 A | 6/1996 | Dumoulin et al. |
| 5,550,953 A | 8/1996 | Seraji |
| 5,669,876 A | 9/1997 | Schechter et al. |
| 5,672,877 A | 9/1997 | Liebig et al. |
| 5,769,086 A | 6/1998 | Ritchart |
| 5,831,614 A | 11/1998 | Tognazzini et al. |
| 5,876,325 A | 3/1999 | Mizuno et al. |
| 5,899,851 A | 5/1999 | Koninckx |
| 5,935,075 A | 8/1999 | Casscells |
| 6,004,016 A | 12/1999 | Spector |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,198,974 B1 | 3/2001 | Webster, Jr. |
| 6,203,493 B1 | 3/2001 | Ben-Haim |
| 6,246,200 B1 | 6/2001 | Blumenkranz et al. |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,459,926 B1 | 10/2002 | Nowlin |
| 6,466,198 B1 | 10/2002 | Feinstein |
| 6,490,467 B1 | 12/2002 | Bucholz |
| 6,553,251 B1 | 4/2003 | Lahdesmaki |
| 6,665,554 B1 | 12/2003 | Charles |
| 6,671,538 B1 | 12/2003 | Ehnholm et al. |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,837,846 B2 | 1/2005 | Jaffe |
| 6,899,672 B2 | 5/2005 | Chin |
| 6,926,709 B2 | 8/2005 | Beiger et al. |
| 7,180,976 B2 | 2/2007 | Wink |
| 7,197,354 B2 | 3/2007 | Sobe |
| 7,206,627 B2 | 4/2007 | Abovitz |
| 7,233,820 B2 | 6/2007 | Gilboa |
| 7,386,339 B2 | 6/2008 | Strommer et al. |
| 7,607,440 B2 | 10/2009 | Coste-Maniere et al. |
| 7,756,563 B2 | 7/2010 | Higgins |
| 7,763,015 B2 | 7/2010 | Cooper et al. |
| 7,772,541 B2 | 8/2010 | Froggatt et al. |
| 7,850,642 B2 | 12/2010 | Moll et al. |
| 7,901,348 B2 | 3/2011 | Soper |
| 7,963,288 B2 | 6/2011 | Rosenberg et al. |
| 8,021,326 B2 | 9/2011 | Moll et al. |
| 8,155,403 B2 | 4/2012 | Tschirren |
| 8,190,238 B2 | 5/2012 | Moll et al. |
| 8,298,135 B2 | 10/2012 | Ito et al. |
| 8,317,746 B2 | 11/2012 | Sewell et al. |
| 8,335,557 B2 | 12/2012 | Maschke |
| 8,348,931 B2 | 1/2013 | Cooper et al. |
| 8,376,934 B2 | 2/2013 | Takahashi |
| 8,394,054 B2 | 3/2013 | Wallace et al. |
| 8,396,595 B2 | 3/2013 | Dariush |
| 8,442,618 B2 | 5/2013 | Strommer et al. |
| 8,460,236 B2 | 6/2013 | Roelle et al. |
| 8,469,945 B2 | 6/2013 | Schena |
| 8,498,691 B2 | 7/2013 | Moll et al. |
| 8,506,555 B2 | 8/2013 | Ruiz Morales |
| 8,554,368 B2 | 10/2013 | Fielding et al. |
| 8,573,228 B2 | 11/2013 | Kalpin |
| 8,652,030 B2 | 2/2014 | Matsuura et al. |
| 8,720,448 B2 | 5/2014 | Reis et al. |
| 8,738,181 B2 | 5/2014 | Greer et al. |
| 8,821,376 B2 | 9/2014 | Tolkowsky |
| 8,827,948 B2 | 9/2014 | Romo et al. |
| 8,858,424 B2 | 10/2014 | Hasegawa |
| 8,894,610 B2 | 11/2014 | MacNamara et al. |
| 8,929,631 B2 | 1/2015 | Pfister et al. |
| 8,945,095 B2 | 2/2015 | Blumenkranz |
| 9,014,851 B2 | 4/2015 | Wong et al. |
| 9,023,060 B2 | 5/2015 | Cooper et al. |
| 9,084,623 B2 | 7/2015 | Gomez et al. |
| 9,125,639 B2 | 9/2015 | Mathis |
| 9,129,417 B2 | 9/2015 | Zheng et al. |
| 9,138,129 B2 | 9/2015 | Diolaiti |
| 9,173,713 B2 | 11/2015 | Hart et al. |
| 9,183,354 B2 | 11/2015 | Baker et al. |
| 9,186,046 B2 | 11/2015 | Ramamurthy et al. |
| 9,199,372 B2 | 12/2015 | Henderson et al. |
| 9,226,796 B2 | 1/2016 | Bowling |
| 9,256,940 B2 | 2/2016 | Carelsen et al. |
| 9,259,274 B2 | 2/2016 | Prisco |
| 9,272,416 B2 | 3/2016 | Hourtash et al. |
| 9,289,578 B2 | 3/2016 | Walker et al. |
| 9,302,702 B1 | 4/2016 | Schepmann |
| 9,314,306 B2 | 4/2016 | Yu |
| 9,345,456 B2 | 5/2016 | Tsonton et al. |
| 9,358,682 B2 | 6/2016 | Ruiz Morales |
| 9,452,276 B2 | 9/2016 | Duindam et al. |
| 9,459,087 B2 | 10/2016 | Dunbar |
| 9,504,604 B2 | 11/2016 | Alvarez |
| 9,522,034 B2 | 12/2016 | Johnson |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,595 B2 | 4/2017 | Walker et al. |
| 9,629,682 B2 | 4/2017 | Wallace et al. |
| 9,636,184 B2 | 5/2017 | Lee et al. |
| 9,668,768 B2 | 6/2017 | Piron et al. |
| 9,675,422 B2 | 6/2017 | Hourtash et al. |
| 9,710,921 B2 | 7/2017 | Wong et al. |
| 9,713,509 B2 | 7/2017 | Schuh et al. |
| 9,717,563 B2 * | 8/2017 | Tognaccini ........ A61B 1/00183 |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,782,229 B2 | 10/2017 | Crawford |
| 9,788,910 B2 | 10/2017 | Schuh |
| 9,789,608 B2 | 10/2017 | Itkowitz et al. |
| 9,839,481 B2 | 12/2017 | Blumenkranz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |

(56) References Cited

U.S. PATENT DOCUMENTS

| | | |
|---|---|---|
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,278,778 B2 | 5/2019 | State |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,492,741 B2 | 10/2019 | Walker et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,531,864 B2 | 1/2020 | Wong et al. |
| 10,539,478 B2 | 1/2020 | Lin |
| 10,543,048 B2 | 1/2020 | Noonan et al. |
| 10,548,666 B2 | 2/2020 | Girotto et al. |
| 10,555,778 B2 | 2/2020 | Ummalaneni et al. |
| 10,583,271 B2 | 3/2020 | Bogusky |
| 10,631,949 B2 | 4/2020 | Schuh et al. |
| 10,639,109 B2 | 5/2020 | Bovay et al. |
| 10,646,291 B2 | 5/2020 | Turner |
| 11,135,023 B2 | 10/2021 | Larkin et al. |
| 11,172,895 B2 | 11/2021 | Dickhans et al. |
| 11,602,372 B2 | 3/2023 | Plewe et al. |
| 11,660,147 B2 | 5/2023 | Ayvali et al. |
| 2001/0000040 A1 | 3/2001 | Adams et al. |
| 2001/0021843 A1 | 9/2001 | Bosselmann et al. |
| 2001/0039421 A1 | 11/2001 | Heilbrun |
| 2002/0035330 A1 | 3/2002 | Cline |
| 2002/0065455 A1 | 5/2002 | Ben-Haim et al. |
| 2002/0077533 A1 | 6/2002 | Bieger et al. |
| 2002/0082612 A1 | 6/2002 | Moll et al. |
| 2002/0120188 A1 | 8/2002 | Brock et al. |
| 2002/0128535 A1 | 9/2002 | Kikuchi |
| 2002/0161280 A1 | 10/2002 | Chatenever et al. |
| 2002/0173878 A1 | 11/2002 | Watanabe |
| 2003/0045778 A1 | 3/2003 | Ohline |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0182091 A1 | 9/2003 | Kukuk |
| 2003/0195664 A1 | 10/2003 | Nowlin et al. |
| 2004/0015079 A1 | 1/2004 | Berger et al. |
| 2004/0047044 A1 | 3/2004 | Dalton |
| 2004/0072066 A1 | 4/2004 | Cho et al. |
| 2004/0152970 A1 | 8/2004 | Hunter et al. |
| 2004/0176751 A1 | 9/2004 | Weitzner et al. |
| 2004/0186349 A1 | 9/2004 | Ewers |
| 2004/0249267 A1 | 12/2004 | Gilboa |
| 2004/0257021 A1 | 12/2004 | Chang et al. |
| 2004/0263535 A1 | 12/2004 | Birkenbach et al. |
| 2005/0027397 A1 | 2/2005 | Niemeyer |
| 2005/0043718 A1 | 2/2005 | Madhani |
| 2005/0060006 A1 | 3/2005 | Pflueger |
| 2005/0065400 A1 | 3/2005 | Banik |
| 2005/0085714 A1 | 4/2005 | Foley et al. |
| 2005/0107679 A1 | 5/2005 | Geiger |
| 2005/0107917 A1 | 5/2005 | Smith et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0222554 A1 | 10/2005 | Wallace et al. |
| 2005/0234293 A1 | 10/2005 | Yamamoto |
| 2005/0256398 A1 | 11/2005 | Hastings |
| 2005/0261551 A1 | 11/2005 | Couvillon |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0041293 A1 | 2/2006 | Mehdizadeh |
| 2006/0058617 A1 | 3/2006 | Sano et al. |
| 2006/0058643 A1 | 3/2006 | Florent |
| 2006/0079745 A1 | 4/2006 | Viswanathan |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0178556 A1 | 8/2006 | Hasser et al. |
| 2006/0184016 A1 | 8/2006 | Glossop |
| 2006/0200026 A1 | 9/2006 | Wallace et al. |
| 2006/0200049 A1 | 9/2006 | Leo et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2006/0287769 A1 | 12/2006 | Yanagita et al. |
| 2007/0013336 A1 | 1/2007 | Nowlin et al. |
| 2007/0032826 A1 | 2/2007 | Schwartz |
| 2007/0043455 A1 | 2/2007 | Viswanathan |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0142971 A1 | 6/2007 | Schena |
| 2007/0150155 A1 | 6/2007 | Kawai |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0185377 A1 | 8/2007 | Murakami et al. |
| 2007/0208252 A1 | 9/2007 | Makower |
| 2007/0232856 A1 | 10/2007 | Ueno |
| 2007/0232882 A1 | 10/2007 | Glossop et al. |
| 2007/0249911 A1 | 10/2007 | Simon |
| 2007/0253599 A1 | 11/2007 | White et al. |
| 2007/0269001 A1 | 11/2007 | Maschke |
| 2007/0287992 A1 | 12/2007 | Diolaiti |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0108870 A1 | 5/2008 | Wiita et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0140087 A1 | 6/2008 | Barbagli et al. |
| 2008/0147089 A1 | 6/2008 | Loh |
| 2008/0159653 A1 | 7/2008 | Dunki-Jacobs et al. |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0231221 A1 | 9/2008 | Ogawa |
| 2008/0243142 A1 | 10/2008 | Gildenberg |
| 2008/0249640 A1 | 10/2008 | Vittor et al. |
| 2008/0255505 A1 | 10/2008 | Carlson et al. |
| 2008/0262297 A1 | 10/2008 | Gilboa |

(56) References Cited

U.S. PATENT DOCUMENTS

| | | |
|---|---|---|
| 2008/0275349 A1 | 11/2008 | Halperin |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2008/0312771 A1 | 12/2008 | Sugiura |
| 2009/0005768 A1 | 1/2009 | Sharareh |
| 2009/0030307 A1 | 1/2009 | Govari |
| 2009/0048611 A1 | 2/2009 | Funda |
| 2009/0054729 A1 | 2/2009 | Mori |
| 2009/0062611 A1 | 3/2009 | Toyama |
| 2009/0062813 A1 | 3/2009 | Prisco |
| 2009/0076476 A1 | 3/2009 | Barbagli et al. |
| 2009/0076534 A1 | 3/2009 | Shelton |
| 2009/0082782 A1 | 3/2009 | Kalpin |
| 2009/0149867 A1 | 6/2009 | Glozman |
| 2009/0184825 A1 | 7/2009 | Anderson |
| 2009/0198298 A1 | 8/2009 | Kaiser et al. |
| 2009/0221908 A1 | 9/2009 | Glossop |
| 2009/0227861 A1 | 9/2009 | Ganatra |
| 2009/0228020 A1 | 9/2009 | Wallace et al. |
| 2009/0245600 A1 | 10/2009 | Hoffman |
| 2009/0248036 A1 | 10/2009 | Hoffman et al. |
| 2009/0256905 A1 | 10/2009 | Tashiro |
| 2009/0259099 A1 | 10/2009 | Zhou et al. |
| 2009/0259230 A1 | 10/2009 | Khadem |
| 2009/0262109 A1 | 10/2009 | Markowitz et al. |
| 2009/0287354 A1 | 11/2009 | Choi |
| 2009/0292166 A1 | 11/2009 | Ito |
| 2009/0295797 A1 | 12/2009 | Sakaguchi |
| 2009/0324161 A1 | 12/2009 | Prisco |
| 2009/0326318 A1 | 12/2009 | Tognaccini |
| 2010/0008555 A1 | 1/2010 | Trumer |
| 2010/0030061 A1 | 2/2010 | Canfield |
| 2010/0030115 A1 | 2/2010 | Fujimoto |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0069920 A1 | 3/2010 | Naylor et al. |
| 2010/0076263 A1 | 3/2010 | Tanaka |
| 2010/0076305 A1 | 3/2010 | Maier-Hein et al. |
| 2010/0082041 A1 | 4/2010 | Prisco |
| 2010/0100045 A1 | 4/2010 | Pravongviengkham et al. |
| 2010/0113852 A1 | 5/2010 | Sydora |
| 2010/0121138 A1 | 5/2010 | Goldenberg et al. |
| 2010/0121139 A1 | 5/2010 | OuYang |
| 2010/0137882 A1* | 6/2010 | Quaid, III ............... A61B 34/70 606/130 |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0168918 A1 | 7/2010 | Zhao |
| 2010/0198170 A1 | 8/2010 | Umeda et al. |
| 2010/0204713 A1 | 8/2010 | Ruiz |
| 2010/0225209 A1 | 9/2010 | Goldberg |
| 2010/0228266 A1 | 9/2010 | Hourtash |
| 2010/0234856 A1 | 9/2010 | Stoianovici et al. |
| 2010/0234857 A1 | 9/2010 | Itkowitz |
| 2010/0240989 A1 | 9/2010 | Stoianovici |
| 2010/0256812 A1 | 10/2010 | Tsusaka et al. |
| 2010/0274087 A1 | 10/2010 | Diolaiti et al. |
| 2010/0290530 A1 | 11/2010 | Huang et al. |
| 2010/0292565 A1 | 11/2010 | Meyer |
| 2010/0298641 A1 | 11/2010 | Tanaka |
| 2010/0298704 A1 | 11/2010 | Pelissier et al. |
| 2010/0328455 A1 | 12/2010 | Nam et al. |
| 2011/0009880 A1 | 1/2011 | Prisco |
| 2011/0015484 A1 | 1/2011 | Alvarez et al. |
| 2011/0021926 A1 | 1/2011 | Spencer |
| 2011/0054303 A1 | 3/2011 | Barrick |
| 2011/0060214 A1 | 3/2011 | Makower |
| 2011/0082366 A1 | 4/2011 | Scully et al. |
| 2011/0082462 A1 | 4/2011 | Suarez |
| 2011/0092808 A1 | 4/2011 | Shachar |
| 2011/0137122 A1 | 6/2011 | Kawai |
| 2011/0153252 A1 | 6/2011 | Govari |
| 2011/0160570 A1 | 6/2011 | Kariv |
| 2011/0184238 A1 | 7/2011 | Higgins |
| 2011/0196199 A1 | 8/2011 | Donhowe et al. |
| 2011/0218676 A1 | 9/2011 | Okazaki |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0258842 A1 | 10/2011 | Dukesherer et al. |
| 2011/0270084 A1 | 11/2011 | Choi et al. |
| 2011/0276179 A1 | 11/2011 | Banks et al. |
| 2011/0277775 A1 | 11/2011 | Holop et al. |
| 2011/0282188 A1 | 11/2011 | Burnside et al. |
| 2011/0319910 A1 | 12/2011 | Roelle et al. |
| 2012/0000427 A1 | 1/2012 | Nilsson |
| 2012/0046521 A1 | 2/2012 | Hunter et al. |
| 2012/0046522 A1 | 2/2012 | Naito |
| 2012/0056986 A1 | 3/2012 | Popovic |
| 2012/0059249 A1 | 3/2012 | Verard et al. |
| 2012/0062714 A1 | 3/2012 | Liu |
| 2012/0065481 A1 | 3/2012 | Hunter |
| 2012/0069167 A1 | 3/2012 | Liu et al. |
| 2012/0071752 A1 | 3/2012 | Sewell |
| 2012/0071782 A1 | 3/2012 | Patil et al. |
| 2012/0071822 A1 | 3/2012 | Romo et al. |
| 2012/0071894 A1 | 3/2012 | Tanner et al. |
| 2012/0082351 A1 | 4/2012 | Higgins |
| 2012/0120305 A1 | 5/2012 | Takahashi |
| 2012/0123441 A1 | 5/2012 | Au |
| 2012/0130217 A1 | 5/2012 | Kauphusman et al. |
| 2012/0143268 A1 | 6/2012 | Burroughs |
| 2012/0165656 A1 | 6/2012 | Montag |
| 2012/0191079 A1 | 7/2012 | Moll et al. |
| 2012/0209069 A1 | 8/2012 | Popovic |
| 2012/0209293 A1 | 8/2012 | Carlson |
| 2012/0215094 A1 | 8/2012 | Rahimian et al. |
| 2012/0219185 A1 | 8/2012 | Hu |
| 2012/0221007 A1 | 8/2012 | Batten et al. |
| 2012/0239060 A1 | 9/2012 | Orban, III |
| 2012/0253200 A1* | 10/2012 | Stolka .................... A61B 90/13 600/459 |
| 2012/0253276 A1 | 10/2012 | Govari et al. |
| 2012/0283745 A1 | 11/2012 | Goldberg et al. |
| 2012/0283747 A1 | 11/2012 | Popovic |
| 2012/0289777 A1 | 11/2012 | Chopra |
| 2012/0289783 A1 | 11/2012 | Duindam et al. |
| 2012/0302869 A1* | 11/2012 | Koyrakh ................ A61B 5/062 600/409 |
| 2012/0328077 A1 | 12/2012 | Bouvier |
| 2013/0018306 A1 | 1/2013 | Ludwin |
| 2013/0060146 A1 | 3/2013 | Yang et al. |
| 2013/0085330 A1 | 4/2013 | Ramamurthy et al. |
| 2013/0090530 A1 | 4/2013 | Ramamurthy |
| 2013/0102846 A1 | 4/2013 | Sjostrom |
| 2013/0123580 A1 | 5/2013 | Peters |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle |
| 2013/0172905 A1* | 7/2013 | Iorgulescu ............. A61B 34/20 606/130 |
| 2013/0197357 A1* | 8/2013 | Green ...................... A61B 6/12 600/424 |
| 2013/0204124 A1 | 8/2013 | Duindam |
| 2013/0209208 A1 | 8/2013 | Bailey |
| 2013/0218005 A1 | 8/2013 | Desai |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0274783 A1 | 10/2013 | Wynberg |
| 2013/0303891 A1 | 11/2013 | Chopra |
| 2013/0303892 A1 | 11/2013 | Zhao |
| 2013/0325030 A1 | 12/2013 | Hourtash et al. |
| 2013/0345718 A1 | 12/2013 | Crawford |
| 2014/0001235 A1 | 1/2014 | Shelton, IV |
| 2014/0051049 A1 | 2/2014 | Jarc |

(56) References Cited

U.S. PATENT DOCUMENTS

| | | |
|---|---|---|
| 2014/0058406 A1 | 2/2014 | Tsekos |
| 2014/0107390 A1 | 4/2014 | Brown |
| 2014/0114180 A1 | 4/2014 | Jain |
| 2014/0148808 A1 | 4/2014 | Inkpen et al. |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0180063 A1 | 6/2014 | Zhao |
| 2014/0222207 A1 | 8/2014 | Bowling et al. |
| 2014/0235943 A1 | 8/2014 | Paris |
| 2014/0243801 A1 | 8/2014 | Fanelli et al. |
| 2014/0243849 A1 | 8/2014 | Saglam |
| 2014/0257333 A1 | 9/2014 | Blumenkranz |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0277333 A1 | 9/2014 | Lewis et al. |
| 2014/0296655 A1 | 10/2014 | Akhbardeh et al. |
| 2014/0296657 A1 | 10/2014 | Izmirli |
| 2014/0296870 A1 | 10/2014 | Stern et al. |
| 2014/0309527 A1 | 10/2014 | Namati et al. |
| 2014/0309625 A1 | 10/2014 | Okamoto et al. |
| 2014/0316420 A1 | 10/2014 | Ballard et al. |
| 2014/0343416 A1 | 11/2014 | Panescu |
| 2014/0343569 A1 | 11/2014 | Turner |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0025549 A1 | 1/2015 | Kilroy et al. |
| 2015/0045675 A1 | 2/2015 | Chernomorsky |
| 2015/0051482 A1 | 2/2015 | Liu et al. |
| 2015/0054929 A1 | 2/2015 | Ito et al. |
| 2015/0057498 A1 | 2/2015 | Akimoto |
| 2015/0073266 A1 | 3/2015 | Brannan |
| 2015/0073267 A1 | 3/2015 | Brannan |
| 2015/0088161 A1 | 3/2015 | Hata |
| 2015/0104284 A1 | 4/2015 | Riedel |
| 2015/0119628 A1 | 4/2015 | Bharat et al. |
| 2015/0119645 A1 | 4/2015 | Baldwin |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0150635 A1 | 6/2015 | Kilroy |
| 2015/0150636 A1 | 6/2015 | Hagn et al. |
| 2015/0202015 A1 | 7/2015 | Elhawary |
| 2015/0209056 A1 | 7/2015 | Shoham et al. |
| 2015/0223725 A1 | 8/2015 | Engel |
| 2015/0223832 A1 | 8/2015 | Swaney |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265359 A1 | 9/2015 | Camarillo |
| 2015/0265368 A1 | 9/2015 | Chopra |
| 2015/0265807 A1 | 9/2015 | Park et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0297299 A1 | 10/2015 | Yeung |
| 2015/0305650 A1* | 10/2015 | Hunter ................ A61B 5/1107 600/424 |
| 2015/0311838 A1 | 10/2015 | Moule |
| 2015/0313503 A1 | 11/2015 | Seibel et al. |
| 2015/0342695 A1 | 12/2015 | He |
| 2015/0359597 A1 | 12/2015 | Gombert et al. |
| 2016/0000302 A1 | 1/2016 | Brown |
| 2016/0000414 A1 | 1/2016 | Brown |
| 2016/0000495 A1 | 1/2016 | Elliott |
| 2016/0000520 A1 | 1/2016 | Lachmanovich |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0008033 A1 | 1/2016 | Hawkins et al. |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0075030 A1 | 3/2016 | Takahashi |
| 2016/0081568 A1 | 3/2016 | Kolberg |
| 2016/0100772 A1 | 4/2016 | Ikuma |
| 2016/0111192 A1 | 4/2016 | Suzara |
| 2016/0128781 A1 | 5/2016 | Blohm et al. |
| 2016/0128992 A1 | 5/2016 | Hudson |
| 2016/0166320 A1 | 6/2016 | Ciulla |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0317225 A1 | 11/2016 | Girotto et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0354152 A1* | 12/2016 | Beck ....................... A61B 34/20 |
| 2016/0360947 A1 | 12/2016 | Lida |
| 2016/0360949 A1 | 12/2016 | Hyodo |
| 2016/0372743 A1 | 12/2016 | Cho et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0056215 A1 | 3/2017 | Nagesh et al. |
| 2017/0065351 A1 | 3/2017 | Case et al. |
| 2017/0068796 A1 | 3/2017 | Passerini et al. |
| 2017/0071456 A1 | 3/2017 | Ratnakar |
| 2017/0079725 A1 | 3/2017 | Hoffman |
| 2017/0079726 A1 | 3/2017 | Hoffman |
| 2017/0095299 A1 | 4/2017 | Hendrick |
| 2017/0100197 A1 | 4/2017 | Zubiate |
| 2017/0106904 A1 | 4/2017 | Hanson |
| 2017/0119412 A1* | 5/2017 | Noonan ............... A61B 17/221 |
| 2017/0119481 A1 | 5/2017 | Romo et al. |
| 2017/0135710 A1 | 5/2017 | Hasegawa et al. |
| 2017/0135718 A1 | 5/2017 | Lyons |
| 2017/0135833 A1 | 5/2017 | Syed |
| 2017/0143442 A1 | 5/2017 | Tesar |
| 2017/0165503 A1 | 6/2017 | Hautvast et al. |
| 2017/0181809 A1* | 6/2017 | Panescu ................. A61B 5/055 |
| 2017/0209162 A1 | 6/2017 | Sperry |
| 2017/0189118 A1* | 7/2017 | Chopra ................... A61B 34/30 |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0231647 A1 | 8/2017 | Saunders |
| 2017/0238807 A9 | 8/2017 | Veritkov et al. |
| 2017/0245854 A1 | 8/2017 | Zemlok |
| 2017/0245885 A1 | 8/2017 | Lenker |
| 2017/0251951 A1 | 9/2017 | Hunter et al. |
| 2017/0251988 A1 | 9/2017 | Weber et al. |
| 2017/0258366 A1 | 9/2017 | Tupin |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0296032 A1 | 10/2017 | Li |
| 2017/0296202 A1 | 10/2017 | Brown |
| 2017/0303889 A1 | 10/2017 | Grim |
| 2017/0303941 A1 | 10/2017 | Eisner |
| 2017/0304015 A1 | 10/2017 | Tavallaei et al. |
| 2017/0325715 A1 | 11/2017 | Mehendale et al. |

(56) References Cited

U.S. PATENT DOCUMENTS

| | | |
|---|---|---|
| 2017/0325896 A1 | 11/2017 | Donhowe |
| 2017/0326337 A1 | 11/2017 | Romascanu |
| 2017/0340241 A1 | 11/2017 | Yamada |
| 2017/0340396 A1* | 11/2017 | Romo et al. |
| 2017/0348067 A1 | 12/2017 | Krimsky |
| 2017/0360508 A1 | 12/2017 | Germain et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0064498 A1 | 3/2018 | Kapadia |
| 2018/0098690 A1 | 4/2018 | Iwaki |
| 2018/0098817 A1 | 4/2018 | Nichogi et al. |
| 2018/0169671 A1 | 6/2018 | Winter |
| 2018/0193102 A1* | 7/2018 | Inoue ............... A61B 1/018 |
| 2018/0200015 A1 | 7/2018 | Ng et al. |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0235709 A1 | 8/2018 | Donhowe et al. |
| 2018/0240237 A1 | 8/2018 | Donhowe et al. |
| 2018/0250083 A1 | 9/2018 | Schuh et al. |
| 2018/0250085 A1 | 9/2018 | Simi |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289394 A1 | 10/2018 | Shah |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0325608 A1* | 11/2018 | Kang ............... A61B 17/1671 |
| 2018/0333044 A1 | 11/2018 | Jenkins |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083178 A1 | 3/2019 | Mata et al. |
| 2019/0083183 A1 | 3/2019 | Moll et al. |
| 2019/0086349 A1 | 3/2019 | Nelson |
| 2019/0110839 A1 | 4/2019 | Rafii-Tari et al. |
| 2019/0151148 A1 | 4/2019 | Alvarez et al. |
| 2019/0125164 A1 | 5/2019 | Roelle et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0201105 A1* | 7/2019 | Shelton, IV ............ G01S 17/04 |
| 2019/0209252 A1 | 7/2019 | Walker et al. |
| 2019/0216548 A1 | 7/2019 | Ummalaneni |
| 2019/0216576 A1 | 7/2019 | Eyre |
| 2019/0223958 A1 | 7/2019 | Kohli et al. |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365199 A1 | 12/2019 | Zhao et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0078103 A1* | 3/2020 | Duindam ............... A61B 34/20 |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier et al. |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0246591 A1 | 8/2020 | Bogusky |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0305922 A1 | 10/2020 | Schuh |
| 2020/0305983 A1 | 10/2020 | Yampolsky |
| 2020/0305989 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2021/0196312 A1 | 7/2021 | Plewe et al. |
| 2021/0196399 A1 | 7/2021 | Ayvali et al. |

FOREIGN PATENT DOCUMENTS

| | | |
|---|---|---|
| CN | 1846181 | 10/2006 |
| CN | 1857877 | 11/2006 |
| CN | 101147676 | 3/2008 |
| CN | 101147676 A | 3/2008 |
| CN | 101222882 | 7/2008 |
| CN | 101325920 | 12/2008 |
| CN | 102316817 | 1/2012 |
| CN | 102316817 A | 1/2012 |
| CN | 101325920 B | 2/2012 |
| CN | 102341057 | 2/2012 |
| CN | 102341057 A | 2/2012 |
| CN | 102458295 | 5/2012 |
| CN | 102711586 | 10/2012 |
| CN | 101222882 B | 3/2013 |
| CN | 102973317 | 3/2013 |
| CN | 103565529 | 2/2014 |
| CN | 103705307 | 4/2014 |
| CN | 103735313 | 4/2014 |
| CN | 103767659 | 5/2014 |
| CN | 103813748 | 5/2014 |
| CN | 103930063 | 7/2014 |
| CN | 104684502 | 6/2015 |
| CN | 104758066 | 7/2015 |

(56) References Cited

FOREIGN PATENT DOCUMENTS

| | | |
|---|---|---|
| CN | 105030331 | 11/2015 |
| CN | 105559850 | 5/2016 |
| CN | 105559886 | 5/2016 |
| CN | 105611881 | 5/2016 |
| CN | 106821498 | 6/2017 |
| CN | 107028659 | 8/2017 |
| CN | 108348139 | 7/2018 |
| CN | 104931059 | 9/2018 |
| CN | 109069136 A | 12/2018 |
| DE | 102013100605 | 7/2014 |
| EP | 0 347 098 | 2/1996 |
| EP | 1 250 986 | 10/2002 |
| EP | 1 566 150 | 8/2005 |
| EP | 1 800 593 | 6/2007 |
| EP | 2 158 834 | 3/2010 |
| EP | 2 392 435 | 12/2011 |
| EP | 3 025 630 | 6/2016 |
| EP | 2 615 992 | 7/2016 |
| EP | 3367915 A1 | 9/2018 |
| JP | 2008-528130 | 7/2008 |
| JP | 2008538184 A | 10/2008 |
| JP | 2009-509654 | 3/2009 |
| JP | 2009-524530 | 7/2009 |
| JP | 2011-088260 | 5/2011 |
| JP | 2012502686 | 2/2012 |
| JP | 2013-510662 | 3/2013 |
| JP | 2013510662 A | 3/2013 |
| JP | 2014512876 A | 5/2014 |
| JP | 2015527906 A | 9/2015 |
| JP | 2017094084 A | 6/2017 |
| JP | 2018524031 A | 8/2018 |
| JP | 6388686 B2 | 9/2018 |
| JP | 2019531809 A | 11/2019 |
| KR | 10-2014-0009359 | 1/2014 |
| RU | 2569699 C2 | 11/2015 |
| WO | 0159643 A1 | 8/2001 |
| WO | WO 01/56457 | 8/2001 |
| WO | 02061371 A1 | 8/2002 |
| WO | WO 04/029782 | 4/2004 |
| WO | 2004114037 A2 | 12/2004 |
| WO | WO 05/087128 | 9/2005 |
| WO | 2006079108 A1 | 7/2006 |
| WO | 2006124388 A1 | 11/2006 |
| WO | WO 06/122061 | 11/2006 |
| WO | 2007041094 A1 | 4/2007 |
| WO | WO 09/097461 | 6/2007 |
| WO | 2007114975 A2 | 10/2007 |
| WO | WO 09/120940 | 10/2009 |
| WO | 2010033306 A2 | 3/2010 |
| WO | 2010133733 A1 | 11/2010 |
| WO | WO 10/127162 | 11/2010 |
| WO | WO 11/002215 | 1/2011 |
| WO | 2011058893 A1 | 5/2011 |
| WO | 2011100110 A1 | 8/2011 |
| WO | WO 11/132409 | 10/2011 |
| WO | WO 12/044334 | 4/2012 |
| WO | WO 12/082719 | 6/2012 |
| WO | 2012109760 A1 | 8/2012 |
| WO | 2013039564 A2 | 3/2013 |
| WO | 2013055707 A1 | 4/2013 |
| WO | 2013071071 A1 | 5/2013 |
| WO | 2014005139 A2 | 1/2014 |
| WO | 2014052428 A1 | 4/2014 |
| WO | WO 14/114551 | 7/2014 |
| WO | WO 15/089013 | 6/2015 |
| WO | WO 15/142957 | 9/2015 |
| WO | 2016176549 A1 | 11/2016 |
| WO | WO 17/036774 | 3/2017 |
| WO | WO 17/048194 | 3/2017 |
| WO | WO 17/053698 | 3/2017 |
| WO | WO 17/066108 | 4/2017 |
| WO | 2017075574 A1 | 5/2017 |
| WO | 2017118750 A1 | 7/2017 |
| WO | WO 17/146890 | 8/2017 |
| WO | WO 17/167754 | 10/2017 |
| WO | 2018085287 A1 | 5/2018 |
| WO | WO 18/098477 | 5/2018 |
| WO | 2019198061 A1 | 10/2019 |

OTHER PUBLICATIONS

Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.

Darwiche, 2015, Operative technique and early experience for robotic assisted laparoscopic nephroureterectomy (RALNU) using da Vinci XI, SpringerPlus, 4:298.

Fallavollita et al., 2010, Acquiring multiview C-arm images to assist cardiac ablation procedures, EURASIP Journal on Image and Video Processing, vol. 2010, Article ID 871408, pp. 1-10.

Haigron et al., 2004, Depth-map-based scene analysis for active navigation in virtual angioscopy, IEEE Transactions on Medical Imaging, 23(11):1380-1390.

Kiraly et al., 2002, Three-dimensional Human Airway Segmentation Methods for Clinical Virtual Bronchoscopy, Acad Radiol, 9:1153-1168.

Kiraly et al., Sep. 2004, Three-dimensional path planning for virtual bronchoscopy, IEEE Transactions on Medical Imaging, 23(9):1365-1379.

Konen et al., 1998, The VN-project: endoscopic image processing for neurosurgery, Computer Aided Surgery, 3:1-6.

Kukuk, Oct. 5, 2001, TBNA-protocols: Guiding TransBronchial Needle Aspirations Without a Computer in the Operating Room, MICCAI 2001, 2208:997-1006.

Kumar et al., 2014, Stereoscopic visualization of laparoscope image using depth information from 3D model, Computer methods and programs in biomedicine 113(3):862-868.

Lawton et al., 1999, Ribbons and groups: A thin rod theory for catheters and filaments, J. Phys. A., 1999, 32:1709-1735.

Livatino et al., 2015, Stereoscopic visualization and 3-D technologies in medical endoscopic teleoperation, IEEE.

Luo et al., 2010, Modified hybrid bronchoscope tracking based on sequential monte carlo sampler: Dynamic phantom validation, Asian Conference on Computer Vision. Springer, Berlin, Heidelberg.

Mayo Clinic, Robotic Surgery, https://www.mayoclinic.org/tests-procedures/robotic-surgery/about/pac-20394974?p=1, downloaded from the internet on Jul. 12, 2018, 2 pp.

Mourgues et al., 2002, Flexible calibration of actuated stereoscopic endoscope for overlay in robot assisted surgery, International Conference on Medical Image Computing and Computer-Assisted Intervention. Springer, Berlin, Heidelberg.

Nadeem et al., 2016, Depth Reconstruction and Computer-Aided Polyp Detection in Optical Colonoscopy Video Frames, arXiv preprint arXiv:1609.01329.

Point Cloud, Sep. 10, 2010, Wikipedia, 2 pp.

Racadio et al., Dec. 2007, Live 3D guidance in the interventional radiology suite, AJR, 189:W357-W364.

Sasaki, 2017, Laparoscopic hemicolectomy for a patient with situs inversus totalis: a case report, Int. J. Surg. Case Rep. 41:93-96.

Sato et al., 2016, Techniques of stapler-based navigational thoracoscopic segmentectomy using virtual assisted lung mapping (VAL-MAP), Journal of Thoracic Disease, 8(Suppl 9):S716.

Shen et al., 2015, Robust camera localisation with depth reconstruction for bronchoscopic navigation. International Journal of Computer Assisted Radiology and Surgery, 10(6):801-813.

Shi et al., Sep. 14-18, 2014, Simultaneous catheter and environment modeling for trans-catheter aortic valve implantation, IEEE/RSJ International Conference on Intelligent Robots and Systems, pp. 2024-2029.

Solheim et al., May 14, 2009, Navigated resection of giant intracranial meningiomas based on intraoperative 3D ultrasound, Acta Neurochir, 151:1143-1151.

Solomon et al., Dec. 2000, Three-dimensional CT- Guided Bronchoscopy With a Real-Time Electromagnetic Position Sensor A Comparison of Two Image Registration Methods, Chest, 118(6):1783-1787.

(56) References Cited

OTHER PUBLICATIONS

Song et al., 2012, Autonomous and stable tracking of endoscope instrument tools with monocular camera, Advanced Intelligent Mechatronics (AIM), 2012 IEEE-ASME International Conference on. IEEE.
Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. < hal-01230752>.
International search report and written opinion dated Dec. 18, 2019 for PCT/US2019/53600.
Al-Ahmad et al., dated 2005, Early experience with a computerized robotically controlled catheter system, Journal of Interventional Cardiac Electrophysiology, 12:199-202.
Gutierrez et al., Mar. 2008, A practical global distortion correction method for an image intensifier based x-ray fluoroscopy system, Med. Phys, 35(3):997-1007.
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Marrouche et al., dated May 6, 2005, AB32-1, Preliminary human experience using a novel robotic catheter remote control, Heart Rhythm, 2(5):S63.
Oh et al., dated May 2005, P5-75, Novel robotic catheter remote control system: safety and accuracy in delivering RF Lesions in all 4 cardiac chambers, Heart Rhythm, 2(5):S277-S278.
Reddy et al., May 2005, P1-53. Porcine pulmonary vein ablation using a novel robotic catheter control system and real-time integration of CT imaging with electroanatomical mapping, Hearth Rhythm, 2(5):S121.
Slepian, dated 2010, Robotic Catheter Intervention: the Hansen Medical Sensei Robot Catheter System, PowerPoint presentation, 28 pp.
Wilson et al., 2008, a buyer's guide to electromagnetic tracking systems for clinical applications, Proc. of SPCI, 6918:69182B-1 p. 6918B-11.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive wav back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pgs.
Hansen Medical, Inc. Technology Advantages, product brochure, dated as available at http://hansenmedical.com/advantages.aspx on Jul. 13, 2006 (accessed Jun. 25, 2019 using the internet archive way back machine), 1 page.
Verdaasdonk et al., Jan. 23, 2012, Effect of microsecond pulse length and tip shape on explosive bubble formation of 2.78 µm Er, Cr; YSGG and 2.94 µm Er:YAG laser, Proceedings of SPIE, vol. 8221. 12.
Non-Final Office Action for U.S. Appl. No. 17/130,700 dated Apr. 5, 2021, 11 pages.
International Search Report for PCT/IB2020/062360, dated Apr. 1, 2021, 3 pages.
Notice of Allowance for U.S. Appl. No. 17/131,117, dated Feb. 1, 2022, 4 pages.
Search Report for Appl. No. PCT/IB2020/062359, dated Jul. 8, 2021, 3 pages.
Written Opinion for Appl. No. PCT/IB2020/062359, dated Apr. 1, 2021, 3 pages.
Written Opinion for PCT/IB2020/062360, dated Apr. 1, 2021, 3 pages.
Notice of Allowance for U.S. Appl. No. 17/131,117, dated Jan. 20, 2022, 11 pages.
Notice of Allowance for U.S. Appl. No. 17/130,700, dated Jul. 8, 2021, 5 pages.
Notice of allowance for U.S. Appl. No. 17/130,700, dated Oct. 29, 2021, 5 pages.
Office action for U.S. Appl. No. 17/130,700, dated Apr. 5, 2021, 11 pages.
Office Action for U.S. Appl. No. 17/131,117, dated Sep. 15, 2021, 9 pages.
Office Action for U.S. Appl. No. 17/130,700, dated Sep. 15, 2021, 11 pages.
International Preliminary Report on Patentability and Written Opinion for Appl. No. PCT/IB2020/062359, dated Jul. 5, 2022, 4 pages.
International Preliminary Report on Patentability and Written Opinion for Appl. No. PCT/IB2020/062360, dated Jul. 5, 2022, 4 pages.
European Search Report for Appl. No. 19867337.8, dated May 27, 2022, 10 pages.
Notice of Allowance for U.S. Appl. No. 17/130,700, dated Feb. 18, 2022, 5 pages.
Notice of Allowance for U.S. Appl. No. 17/131,117, dated May 11, 2022, 8 pages.
Notice of Allowance for U.S. Appl. No. 17/130,700, dated Jun. 16, 2022, 2 pages.
Notice of Allowance for U.S. Appl. No. 17/130,700, dated Jun. 3, 2022, 5 pages.
Notice of Allowance for Appl. No. 17/111,17, dated Sep. 28, 2022, 8 pages.
Notice of Allowance for U.S. Appl. No. 17/130,700, dated Nov. 3, 2022, 5 pages.
CN Office Action for Appl. No. 202080091047.7, dated Apr. 17, 2023, 8 pages.
JP Office Action for Appl. No. 2021-517238, dated Aug. 10, 2023, 15 pages.
CN Office Action for Appl. No. 202080091047.7, dated Nov. 20, 2023, 11 pages.
Notice of Allowance for U.S. Appl. No. 17/131,117, dated Feb. 8, 2023, 3 pages.
Notice of Allowance for U.S. Appl. No. 17/131,117, dated Jan. 31, 2023, 8 pages.
Anonymous: "Software User Guide Rev. 1.0 Kolibri cranial/ENT Ver. 2.7", Jan. 1, 2010 (Jan. 1, 2010), XP055859399, Retrieved from the Internet: URL: https://manulaslib.com/manual/1863481/Brainlab-Kolibri-Cranial.html [retrieved on Nov. 9, 2021].
CN Office Action for Appl. No. 201980063756.1, dated Dec. 13, 2023, 8 pages.
CN Search Report for Appl. No. 201980063756.1, dated Dec. 1, 2023, 2 pages.
EP Examination Report for Appl. No. 19867337.8, dated Jan. 31, 2024, 6 pages.
EP Search Report for Appl. No. 20909386.3, dated Dec. 18, 2023, 8 pages.
EP Search Report for Appl. No. 20910792.9, dated Dec. 11, 2023, 12 pages.
JP Office Action for Appl. No. 2021-517238, dated Feb. 14, 2024, 17 pages.
JP Office Action for Appl. No. 2022-540452, dated Jan. 26, 2024, 4 pages.
AU Examination Report for Appl. No. 2019347754, dated May 9, 2024, 4 pages.

(56) References Cited

OTHER PUBLICATIONS

CN 2nd Office Action for Appl. No. 201980063756.1, dated May 24, 2024, 8 pages.

* cited by examiner

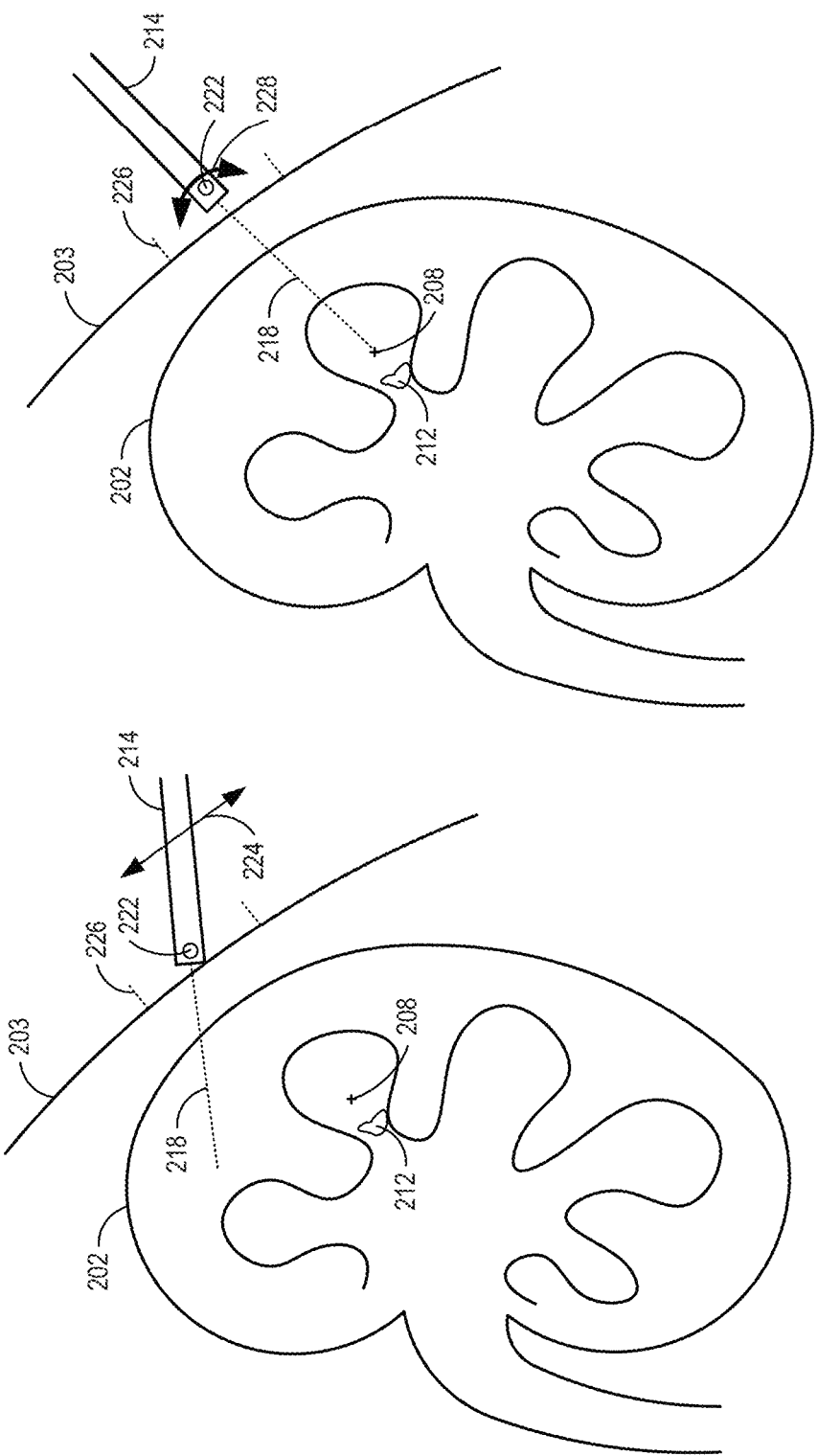

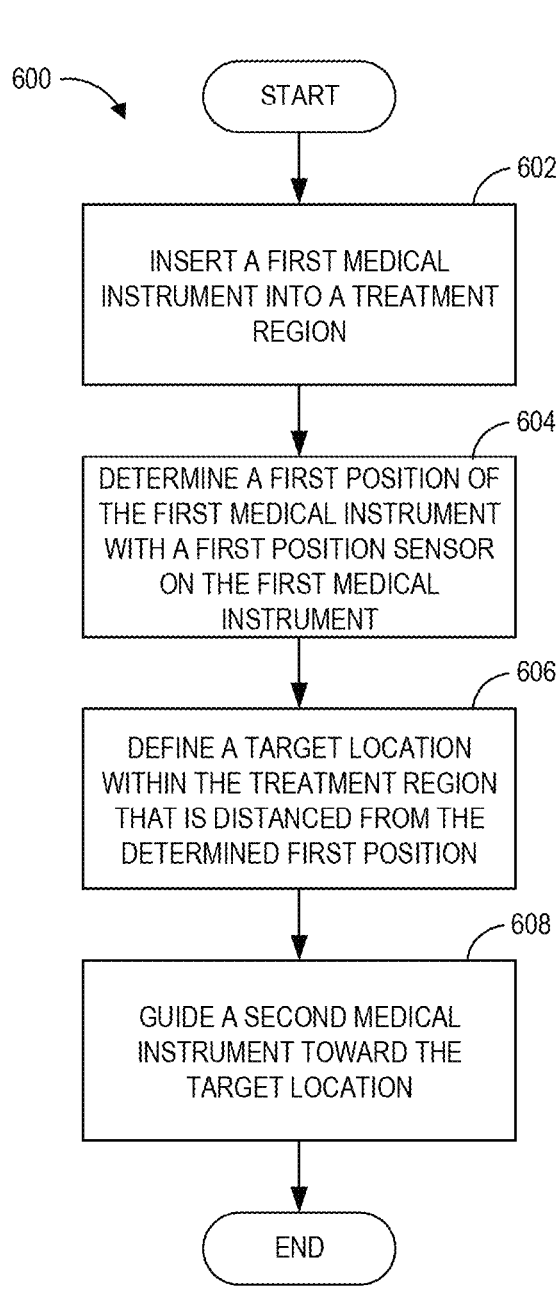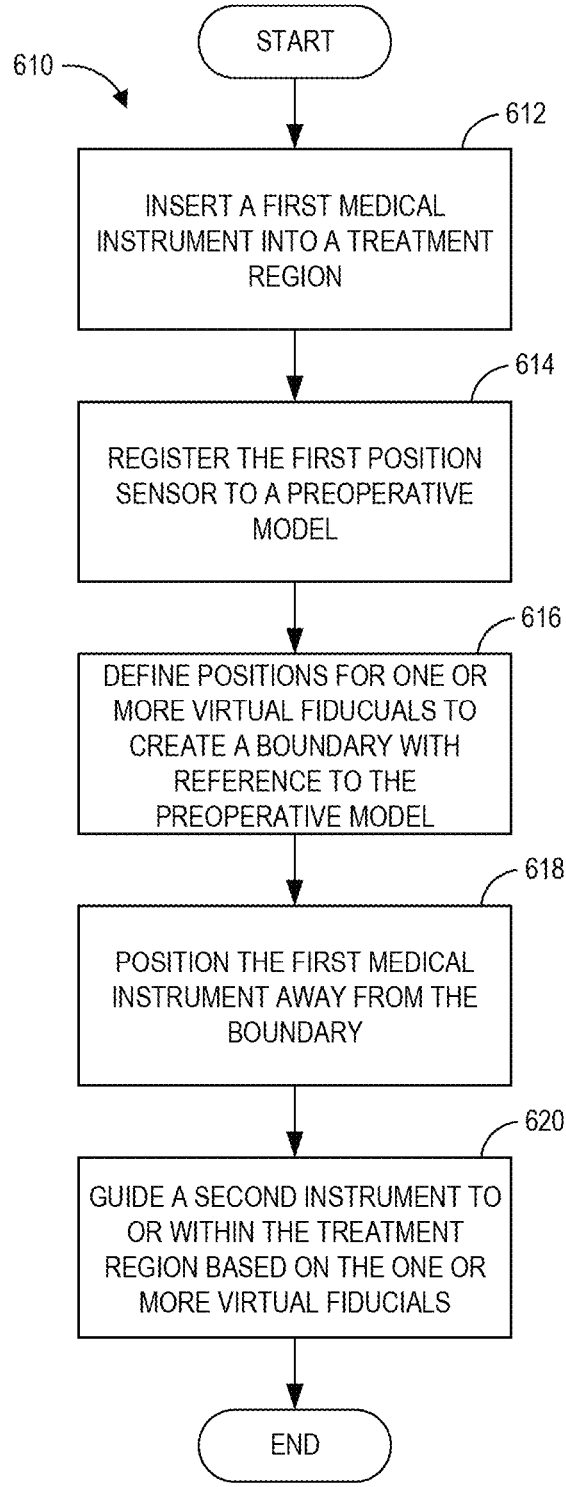
FIG. 27A
FIG. 27B

ROBOTIC SYSTEMS AND METHODS FOR CONCOMITANT ENDOSCOPIC AND PERCUTANEOUS MEDICAL PROCEDURES

PRIORITY APPLICATION(S)

This application claims priority to U.S. Provisional Patent Application No. 62/738,706, filed Sep. 28, 2018, which is incorporated herein by reference. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to medical systems and medical procedures, and more particularly, to robotic systems and methods for concomitant endoscopic and percutaneous medical procedures, such as endoscopically-assisted percutaneous medical procedures and laparoscopically-assisted endoscopic procedures.

BACKGROUND

Medical procedures such as endoscopy and laparoscopy may involve accessing and visualizing the inside of a patient's anatomy for diagnostic and/or therapeutic purposes. For example, ureteroscopy is a medical procedure commonly used for the treatment of kidney stones. During the procedure, a thin, flexible tubular tool or instrument, known as a ureteroscope, may be inserted into the urethra, through the bladder and ureter, and into the kidney. In some instances, percutaneous access to the kidney may also be desired.

In certain medical procedures, surgical robotic systems may be used to control the insertion and/or manipulation of the surgical tools. Surgical robotic systems may include at least one robotic arm or other instrument positioning device including a manipulator assembly used to control the positioning of the surgical tool during the procedures.

SUMMARY

The systems, methods and devices of this disclosure each have several innovative aspects, no single one of which is solely responsible for the desirable attributes disclosed herein.

In a first aspect, a method for performing a medical procedure comprises: inserting a first medical instrument comprising an elongated shaft and a first position sensor into a treatment region of a patient through a natural orifice of the patient; determining a first position of the first medical instrument within the treatment region with the first position sensor; defining a target location within the treatment region that is distanced from the determined first position; and percutaneously guiding a second medical instrument through the patient toward the target location.

The method may also include one or more of the following features in any combination: (a) registering an output of the first position sensor with a coordinate frame of a preoperative model, and wherein determining the first position of the instrument within the treatment region with the first position sensor comprises determining the first position with reference to the preoperative model; (b) wherein the preoperative model comprises a three dimensional reconstruction of anatomy; (c) wherein defining the target location within the treatment region comprises determining the target location with reference to the preoperative model; (d) wherein determining the target location with reference to the preoperative model comprises: displaying the preoperative model to a user, and receiving a selection of the target location with reference to the preoperative model; (e) wherein defining the target location comprises determining, with reference to the preoperative model, a difference between the determined first position and the target location; (f) displaying a representation of the target location to the user; (g) wherein defining the target location within the treatment region comprises: capturing one or more intraoperative medical images of the treatment region, and defining the target location with reference to the one or more intraoperative medical images; (h) wherein the one or more intraoperative medical images comprise one or more fluoroscopic images; (i) registering an output of the first position sensor to the one or more intraoperative medical images; (j) wherein defining the target location within the treatment region that is distanced from the determined first position comprises determining the target location along a first axis that extends from a distal end of the elongated shaft of the first medical instrument; (k) wherein percutaneously guiding the second medical instrument through the patient toward the target location comprises: aligning a second axis of the second medical instrument with the target location, and advancing the second medical instrument toward the target location; (l) wherein: the second medical instrument is attached to a robotic arm; and the robotic arm restricts motion of the second medical instrument to motion along the second axis; (m) wherein the first medical instrument comprises an endoscope; (n) wherein the first medical instrument is robotically controlled; (o) wherein the second medical instrument is robotically controlled; (p) wherein the treatment region comprises a kidney, a bladder, a lung, or a gastrointestinal tract; (q) determining patient movement with the first position sensor of the first medical instrument, and wherein percutaneously guiding the second instrument through the patient toward the target location is based in part on the determined patient movement; and/or (r) wherein the patient movement is due to respiration.

In another aspect, a method for performing a medical procedure comprises: inserting a first medical instrument comprising an elongated shaft and a first position sensor into a treatment region of a patient through a natural orifice of the patient; registering an output of the first position sensor with a coordinate frame of a preoperative model; displaying the preoperative model to a user; defining positions for one or more virtual fiducials to create a boundary with reference to the preoperative model, the positions of the one or more virtual fiducials determined based on the registered output of the first position sensor; positioning the first medical instrument such that the first position sensor is distanced from the boundary; and guiding a second instrument to or within the treatment region through a percutaneous opening based on the one or more virtual fiducials.

The method may also include one or more of the following features in any combination: (a) wherein determining the positions for the one or more virtual fiducials comprises, for each of the positions: navigating the first medical instrument to a location within the treatment region at which a virtual fiducial will be placed, and defining the location as the position of a virtual fiducial based on the registered output of the first position sensor; (b) wherein determining the positions for the one or more virtual fiducials comprises, for each of the positions: receiving a user selection of a location at which to place one of the one more virtual fiducials, and determining a virtual fiducial position corresponding to the location with reference to at least a first position determined based on the first position sensor, wherein the virtual fiducial position is distanced from the first position; (c) wherein the boundary defines a resection volume; (d) wherein the first medical instrument comprises an endoscope; (e) wherein the first medical instrument is robotically controlled; (f) wherein the treatment region comprises a kidney, a bladder, a lung, or a gastrointestinal tract; and/or (g) wherein the preoperative model is determined based on a CT scan.

In another aspect, a computer readable medium comprises instructions configured to cause at least one processor to: insert a first medical instrument comprising an elongated shaft and a first position sensor into a treatment region of a patient through a natural orifice of the patient; determine a first position of the first medical instrument within the treatment region with the first position sensor; define a target location within the treatment region that is distanced from the determined first position; and percutaneously guide a second medical instrument through the patient toward the target location.

The computer readable medium may also include one or more of the following features in any combination: (a) wherein the instructions further cause the at least one processor to register an output of the first position sensor with a coordinate frame of a preoperative model, and wherein determining the first position of the instrument within the treatment region with the first position sensor comprises determining the first position with reference to the preoperative model; (b) wherein the preoperative model comprises a three dimensional reconstruction of anatomy; (c) wherein defining the target location within the treatment region comprises determining the target location with reference to the preoperative model; (d) wherein determining the target location with reference to the preoperative model comprises: displaying the preoperative model to a user, and receiving a selection of the target location with reference to the preoperative mode; (e) wherein defining the target location comprises determining, with reference to the preoperative model, a difference between the determined first position and the target location; (f) wherein the instructions further cause the at least one processor to display a representation of the target location to the user; (g) defining the target location within the treatment region comprises: capturing one or more intraoperative medical images of the treatment region, and defining the target location with reference to the one or more intraoperative medical images; (h) wherein the one or more intraoperative medical images comprise one or more fluoroscopic images; (i) wherein the instructions further cause the at least one processor to register an output of the first position sensor to the one or more intraoperative medical images; (j) wherein defining the target location within the treatment region that is distanced from the determined first position comprises determining the target location along a first axis that extends from a distal end of the elongated shaft of the first medical instrument; (k) wherein percutaneously guiding the second medical instrument through the patient toward the target location comprises: aligning a second axis of the second medical instrument with the target location, and advancing the second medical instrument toward the target location; (l) wherein: the second medical instrument is attached to a robotic arm, the robotic arm restricts motion of the second medical instrument to motion along the second axis; (m) wherein the first medical instrument comprises an endoscope; (n) wherein the first medical instrument is robotically controlled; (o) the second medical instrument is robotically controlled; (p) wherein the treatment region comprises a kidney, a bladder, a lung, or a gastrointestinal tract; (q) wherein the instructions further cause the at least one processor to: determine patient movement with the first position sensor of the first medical instrument, and wherein percutaneously guiding the second instrument through the patient toward the target location is based in part on the determined patient movement; and/or (r) wherein the patient movement is due to respiration.

In another aspect, a medical system comprises: a first medical instrument configured to be inserted into a treatment region of a patient through a natural orifice of the patient, the first medical instrument comprising an elongated shaft and a first position sensor; a second medical instrument configured to be inserted into the treatment region through a percutaneous opening in the patient; at least one computer-readable memory having stored thereon executable instructions; and one or more processors in communication with the at least one computer-readable memory and configured to execute the instructions to cause the system to at least: determine a first position of the first medical instrument within the treatment region based on an output of first position sensor; define a target location within the treatment region that is distanced from the determined first position; register the target location to the determined first position; and guide the second medical instrument through a percutaneous opening toward the target location.

The system may also include one or more of the following features in any combination: (a) wherein the instructions further cause the system to register an output of the first position sensor with a coordinate frame of a preoperative model, and wherein determining the first position of the instrument within the treatment region with the first position sensor comprises determining the first position with reference to the preoperative model; (b) wherein defining the target location within the treatment region comprises determining the target location with reference to the preoperative model; (c) wherein determining the target location with reference to the preoperative model comprises: displaying the preoperative model to a user, and receiving a selection of the target location with reference to the preoperative model; (d) wherein defining the target location comprises determining, with reference to the preoperative model, a difference between the determined first position and the target location; (e) a display configured for displaying a representation of the target location to the use; (f) wherein defining the target location within the treatment region comprises: capturing one or more intraoperative medical images of the treatment region, and defining the target location with reference to the one or more intraoperative medical images; (g) wherein the one or more intraoperative medical images comprise one or more fluoroscopic images; (h) wherein the instructions further cause the system to register an output of the first position sensor to the one or more intraoperative medical images; (i) wherein defining the target location within the treatment region that is distanced from the determined first position comprises determining the target location along a first axis that extends from a distal end of the elongated shaft of the first medical instrument; (j) wherein guiding the second medical instrument through the patient toward the target location comprises: aligning a second axis of the second medical instrument with the target location, and advancing the second medical instrument toward the target location; (k) a robotic arm, wherein the second medical instrument is attached to the robotic arm, and the robotic arm restricts motion of the second medical instrument to motion along the second axis; (l) wherein the first medical instrument comprises an endoscope; (m) wherein the first medical instrument is robotically controlled; and/or (n) wherein the second medical instrument is robotically controlled.

In another aspect, a computer readable medium comprises instructions configured to cause at least one processor to: insert a first medical instrument comprising an elongated shaft and a first position sensor into a treatment region of a patient through a natural orifice of the patient; register an output of the first position sensor with a coordinate frame of a preoperative model; display the preoperative model to a user; define positions for one or more virtual fiducials to create a boundary with reference to the preoperative model, the positions of the one or more virtual fiducials determined based on the registered output of the first position sensor; position the first medical instrument such that the first position sensor is distanced from the boundary; and guide a second instrument to or within the treatment region through a percutaneous opening based on the one or more virtual fiducials.

The computer readable medium may also include one or more of the following features in any combination: (a) wherein determining the positions for the one or more virtual fiducials comprises, for each of the positions: navigating the first medical instrument to a location within the treatment region at which a virtual fiducial will be placed, and defining the location as the position of a virtual fiducial based on the registered output of the first position sensor; (b) wherein determining the positions for the one or more virtual fiducials comprises, for each of the positions: receiving a user selection of a location at which to place one of the one more virtual fiducials, and determining a virtual fiducial position corresponding to the location with reference to at least a first position determined based on the first position sensor, wherein the virtual fiducial position is distanced from the first position; (c) wherein the boundary defines a resection volume; (d) wherein the first medical instrument comprises an endoscope; (e) wherein the first medical instrument is robotically controlled; (f) wherein the treatment region comprises a kidney, a bladder, a lung, or a gastrointestinal tract; and/or (g) wherein the preoperative model is determined based on a CT scan.

In another aspect, a medical system comprises: a first medical instrument configured to be inserted into a treatment region of a patient through a natural orifice of the patient, the first medical instrument comprising an elongated shaft and a first position sensor; a second medical instrument configured to be inserted into the treatment region through a percutaneous opening in the patient; at least one computer-readable memory having stored thereon executable instructions; and one or more processors in communication with the at least one computer-readable memory and configured to execute the instructions to cause the system to at least: register an output of the first position sensor with a coordinate frame of a preoperative model; display the preoperative model to a user; define positions for one or more virtual fiducials to create a boundary with reference to the preoperative model, the positions of the one or more virtual fiducials determined based on the registered output of the first position sensor; and guide the second medical instrument to or within the treatment region through a percutaneous opening based on the one or more virtual fiducials.

The system may also include one or more of the following features in any combination: (a) wherein determining the positions for the one or more virtual fiducials comprises, for each of the positions: navigating the first medical instrument to a location within the treatment region at which a virtual fiducial will be placed, and defining the location as the position of a virtual fiducial based on the registered output of the first position sensor; (b) wherein determining the positions for the one or more virtual fiducials comprises, for each of the positions: receiving a user selection of a location at which to place one of the one more virtual fiducials, and determining a virtual fiducial position corresponding to the location with reference to at least a first position determined based on the first position sensor, wherein the virtual fiducial position is distanced from the first position; (c) wherein the boundary defines a resection volume; (d) wherein the first medical instrument comprises an endoscope; (e) wherein the first medical instrument is robotically controlled; (f) wherein the treatment region comprises a kidney, a bladder, a lung, or a gastrointestinal tract; and/or (g) wherein the preoperative model is determined based on a CT scan.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 21A illustrates an example of a first medical instrument being guided into the kidney.

FIG. 21B illustrates an example of determination of a target location that is distanced from the first medical instrument.

FIG. 21C illustrates an example of alignment of a second medical instrument with the target location.

FIG. 21D illustrates an example of percutaneous insertion of the second medical instrument to arrive at the target location.

FIGS. 22A and 22B illustrate various steps in an embodiment of an alignment method for aligning a medical instrument with a target location for some concomitant endoscopic and percutaneous medical procedures.

FIG. 22A illustrates an example of a gross alignment step during which a distal end of the medical instrument is brought into proximity with the target location.

FIG. 22B illustrates an example of a fine alignment step during which a longitudinal axis of the medical instrument is aligned with the target location.

FIG. 23A illustrates an example of the alignment interface when the medical instrument is not aligned with the target location.

FIG. 23B illustrates an example of the alignment interface when the medical instrument is aligned with the target location.

FIG. 25A illustrates an example of placing or creating virtual fiducials during the procedure.

FIG. 25B illustrates an example of creating a boundary for one or more percutaneous instruments based on the virtual fiducials.

FIG. 27A is a flow chart illustrating an embodiment of a method for performing a medical procedure that includes rendezvousing a medical instrument with a target location.

FIG. 27B is a flow chart illustrating an embodiment of a method for performing a medical procedures that includes placing virtual fiducials to define a boundary.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
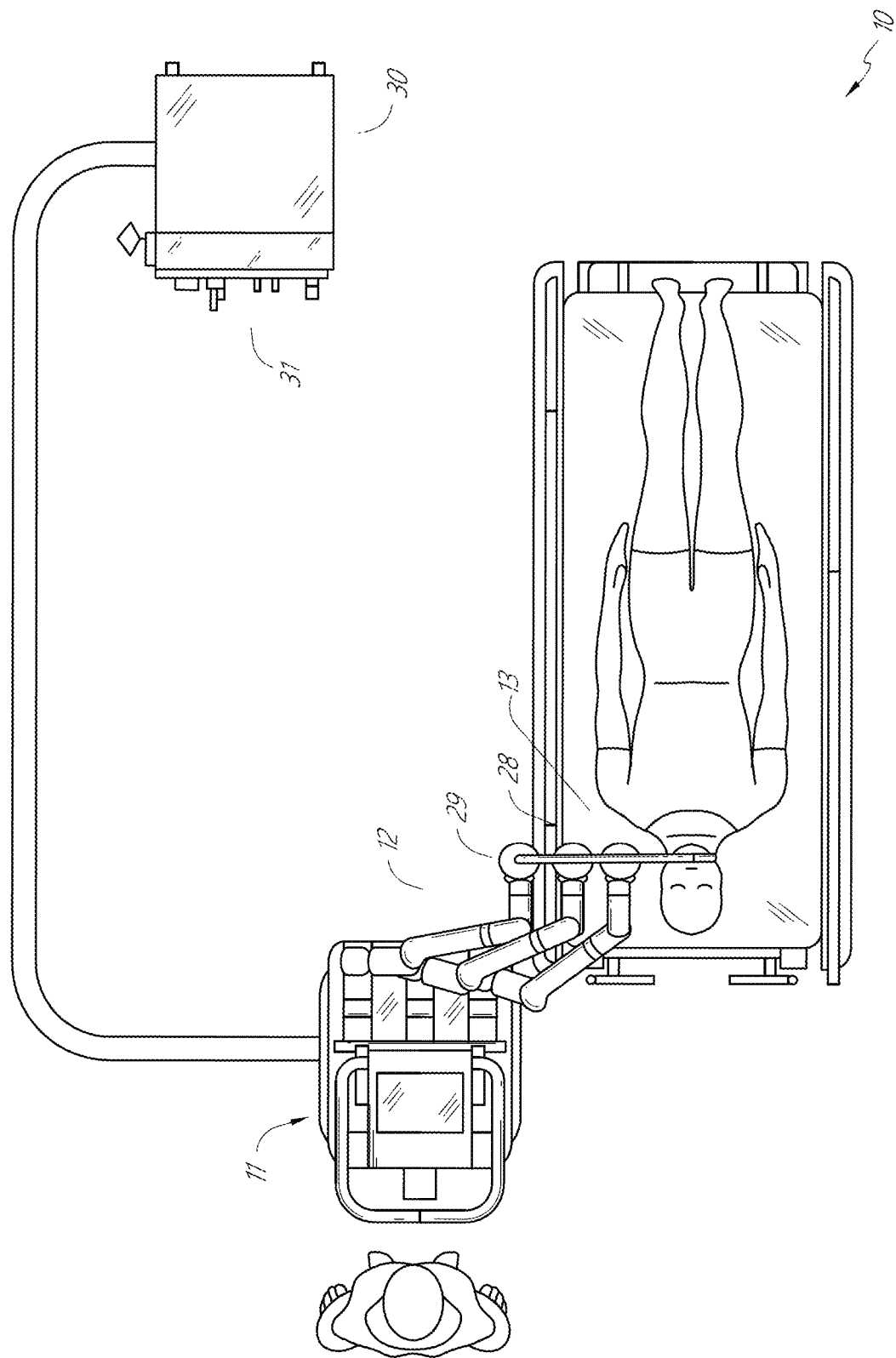
FIG. 1 illustrates an embodiment of a cart-based robotic system arranged for diagnostic and/or therapeutic bronchoscopy.
Figure 2:
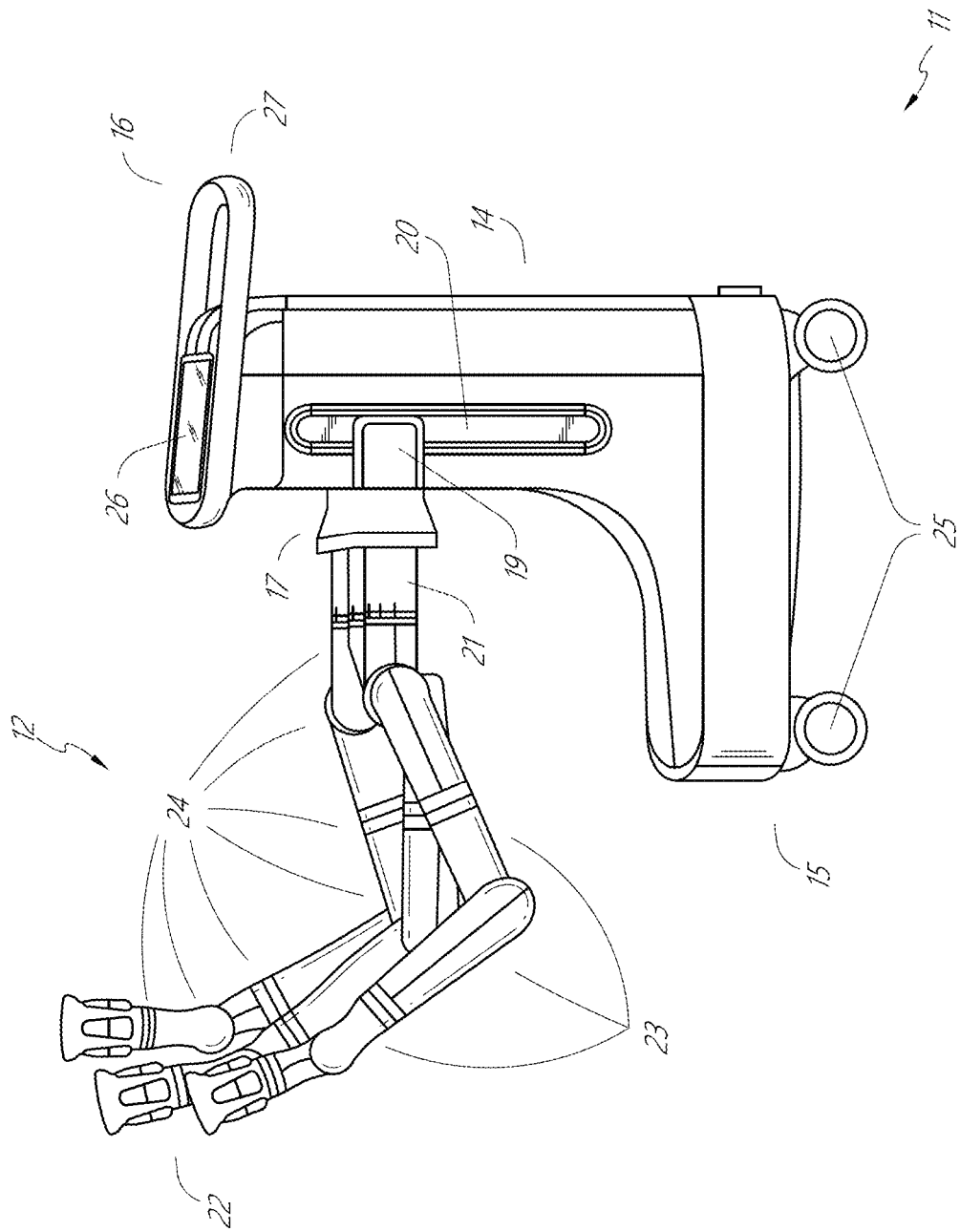
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from pre-operative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
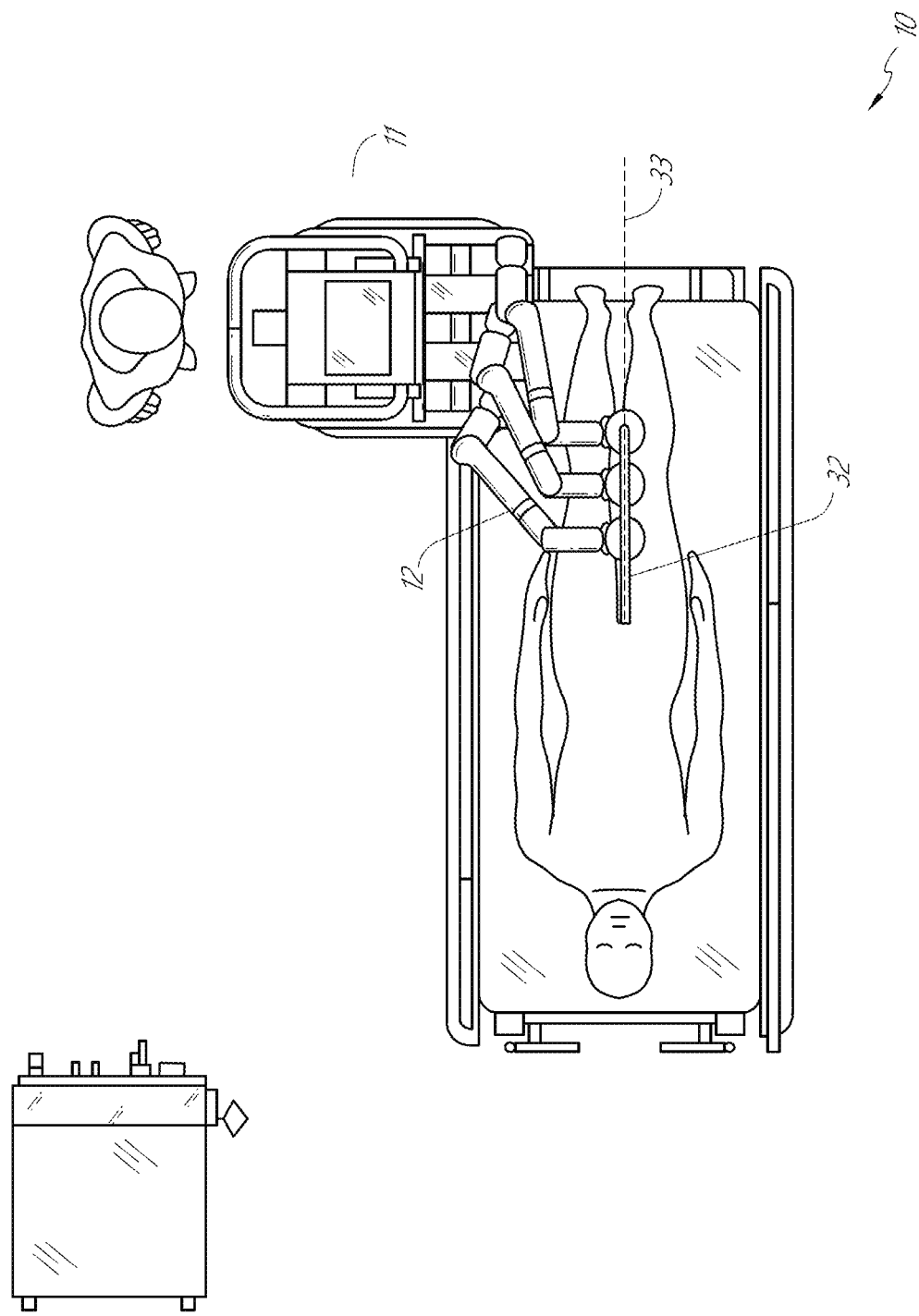
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
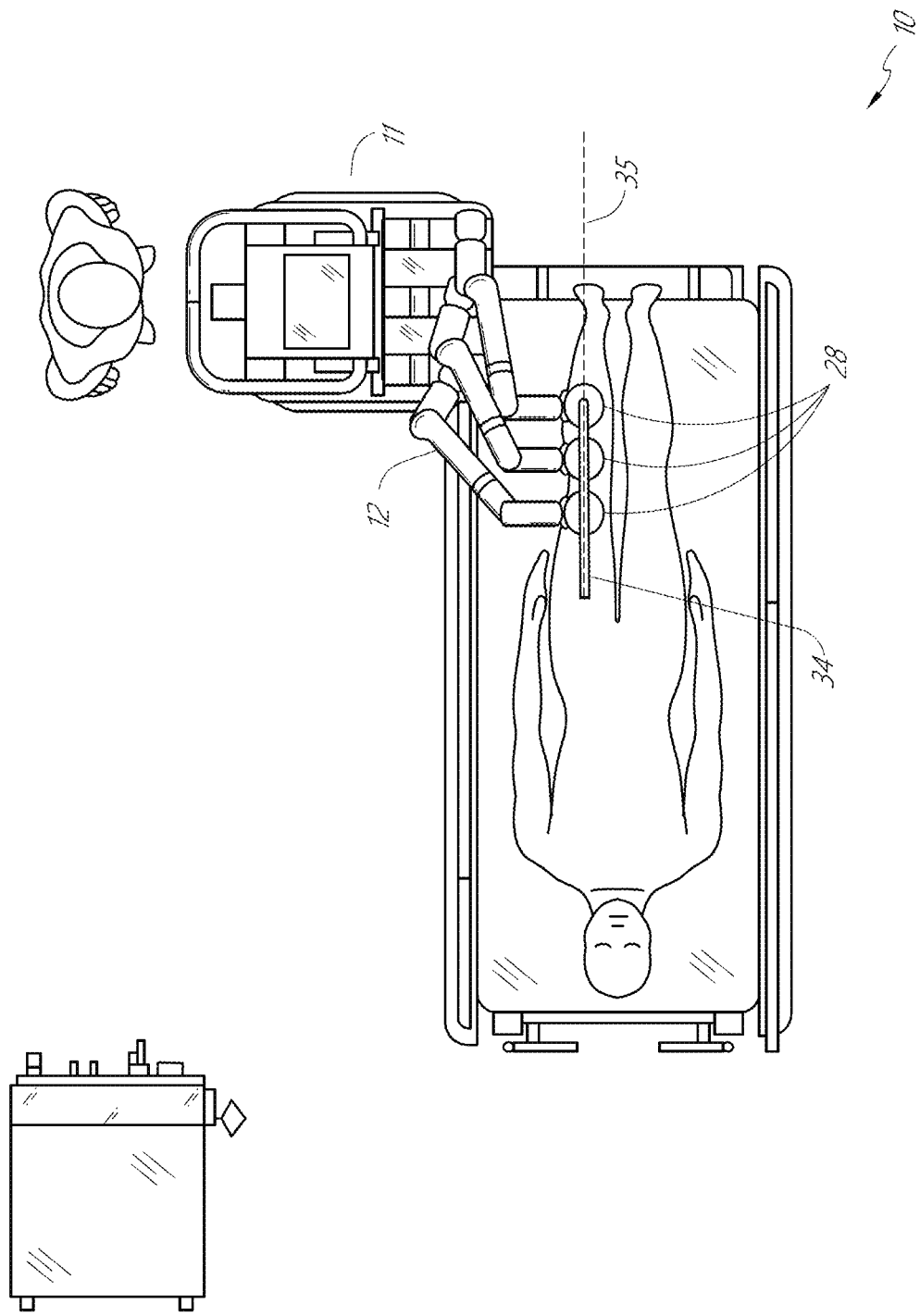
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
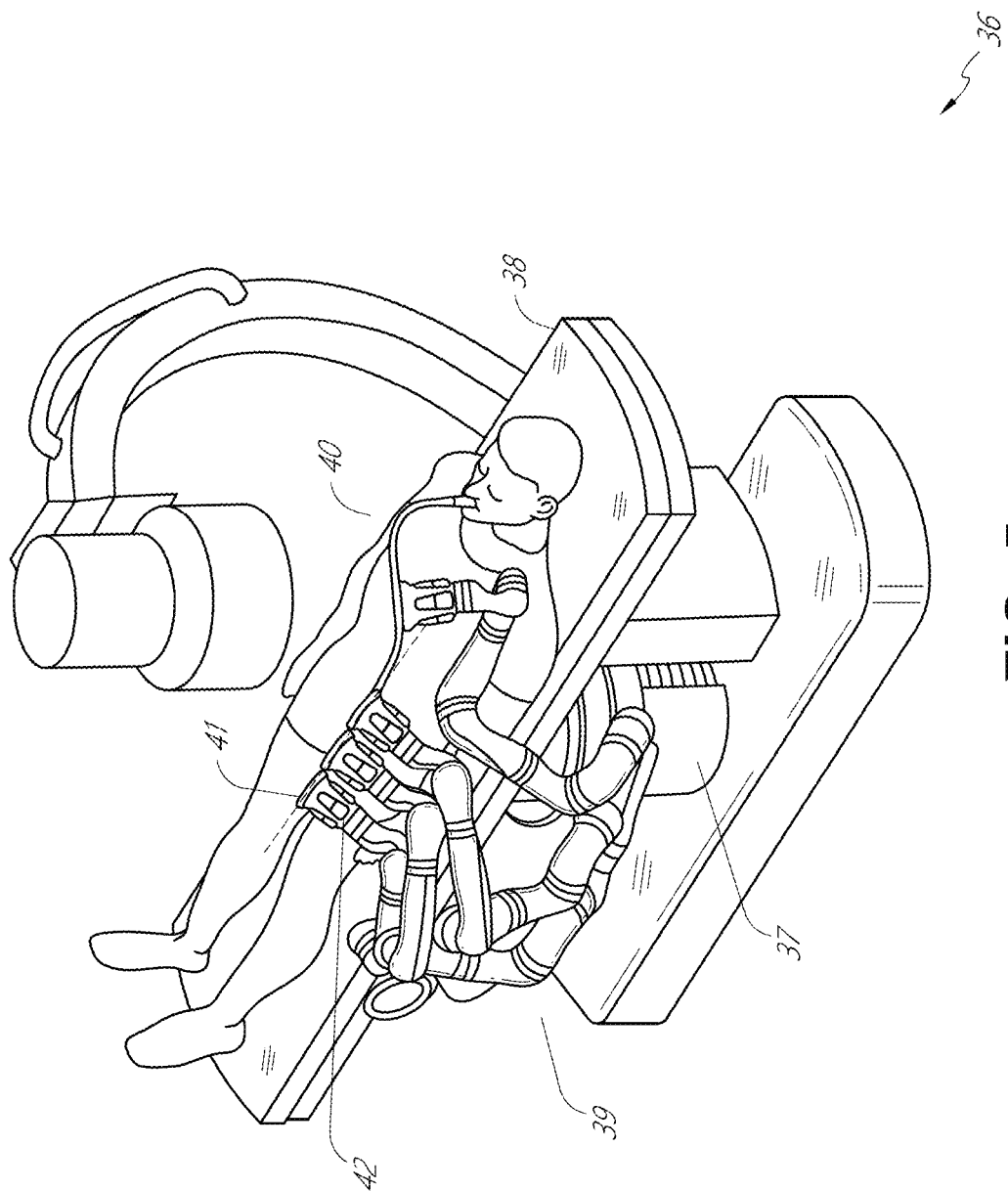
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
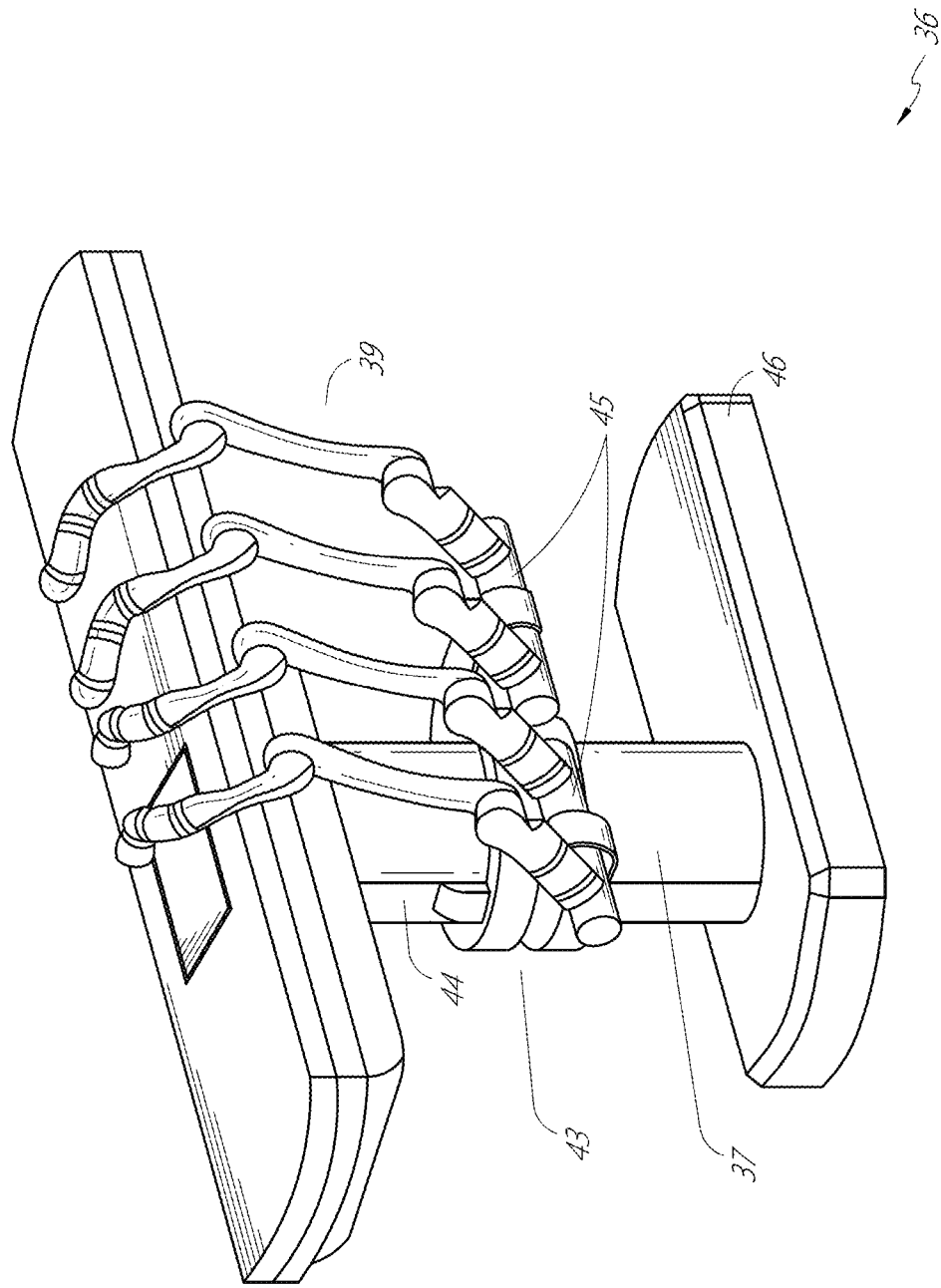
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
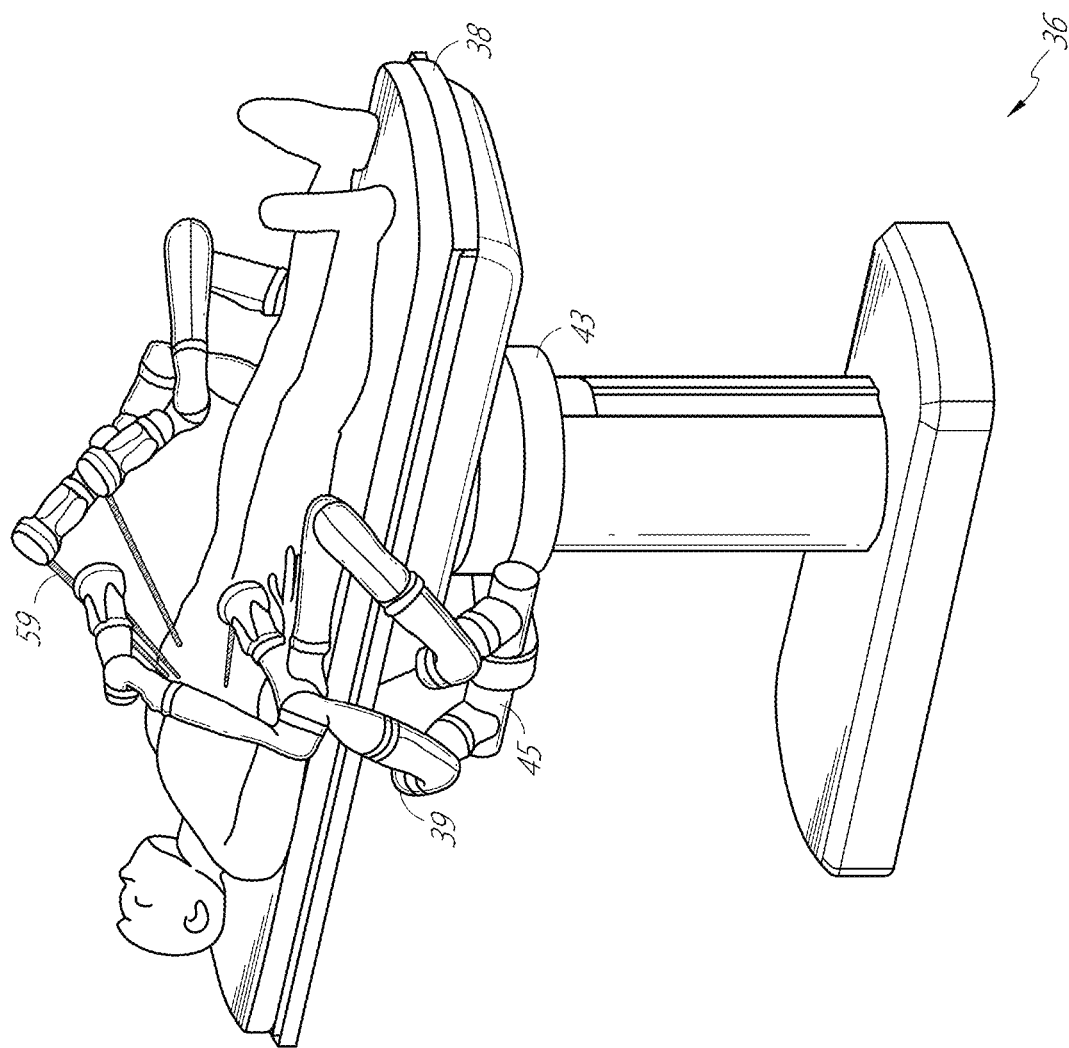
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
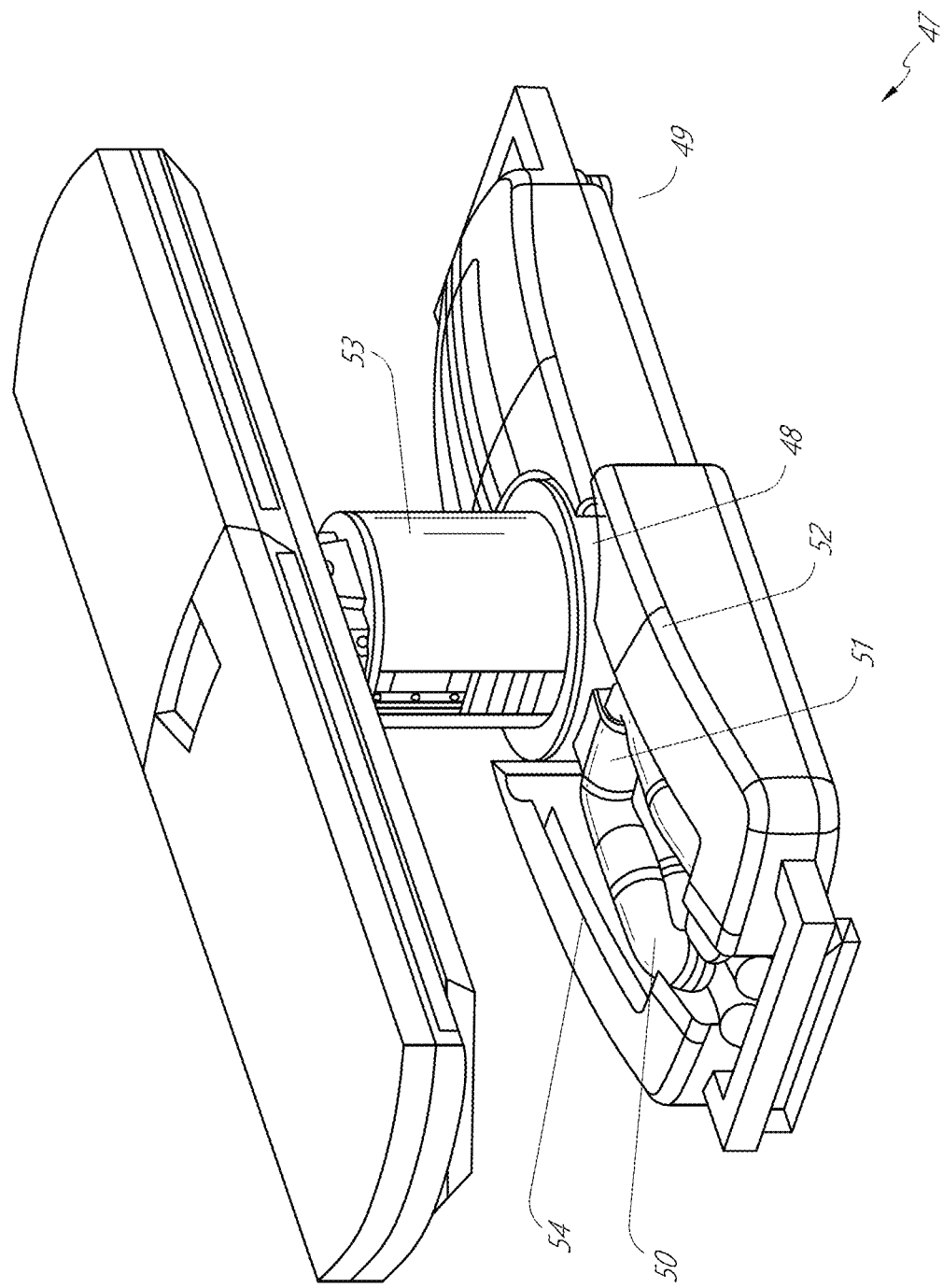
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
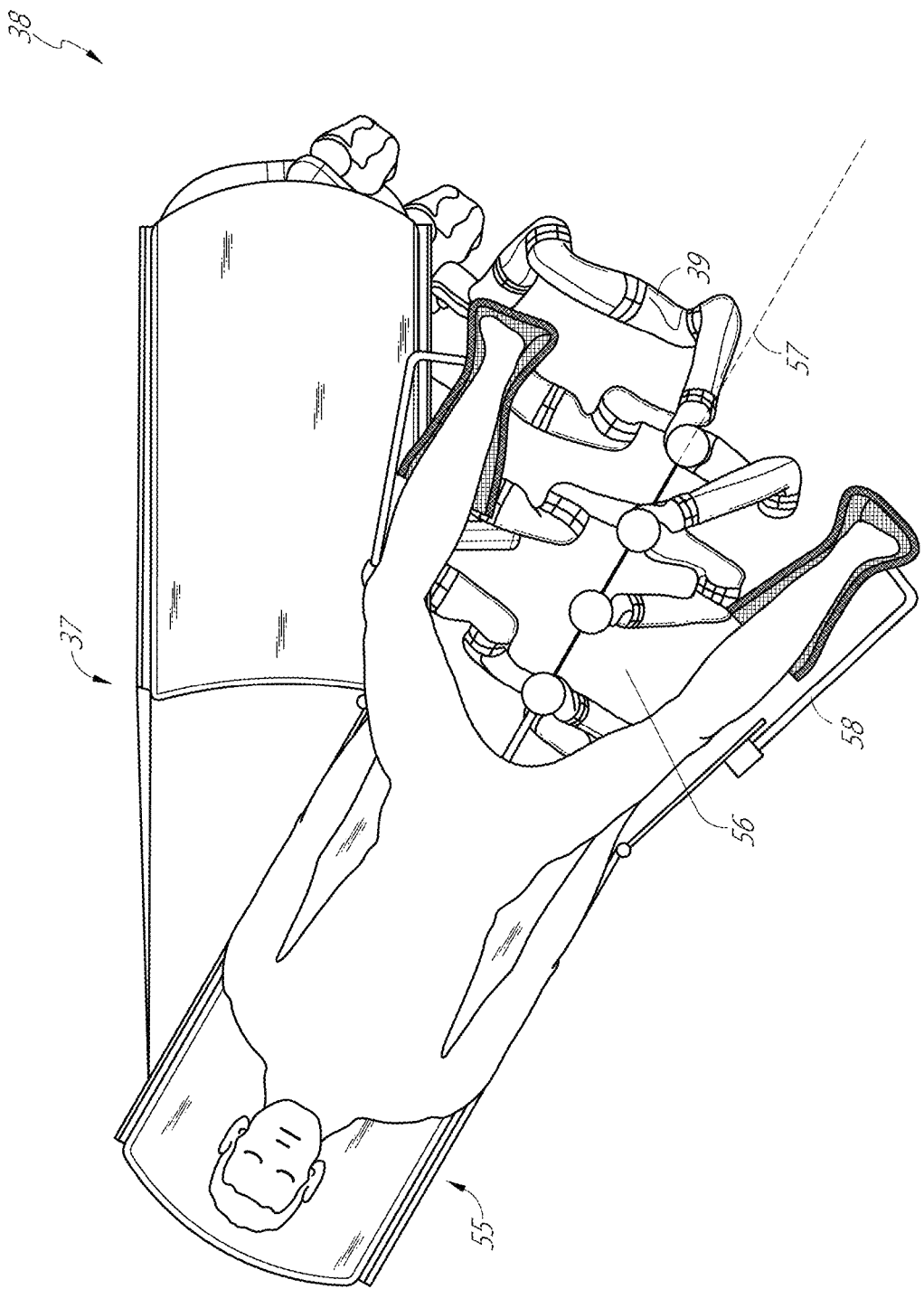
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
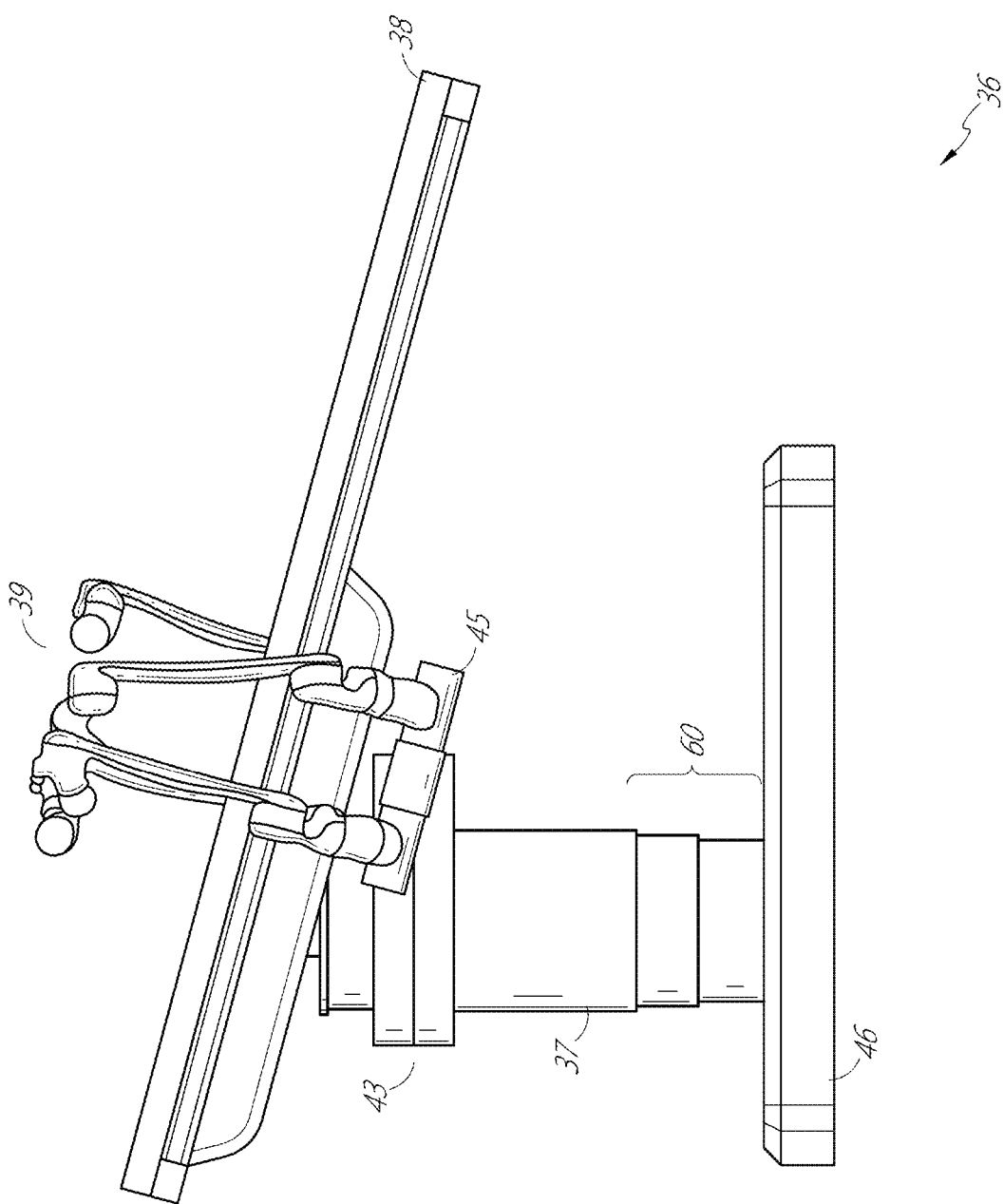
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
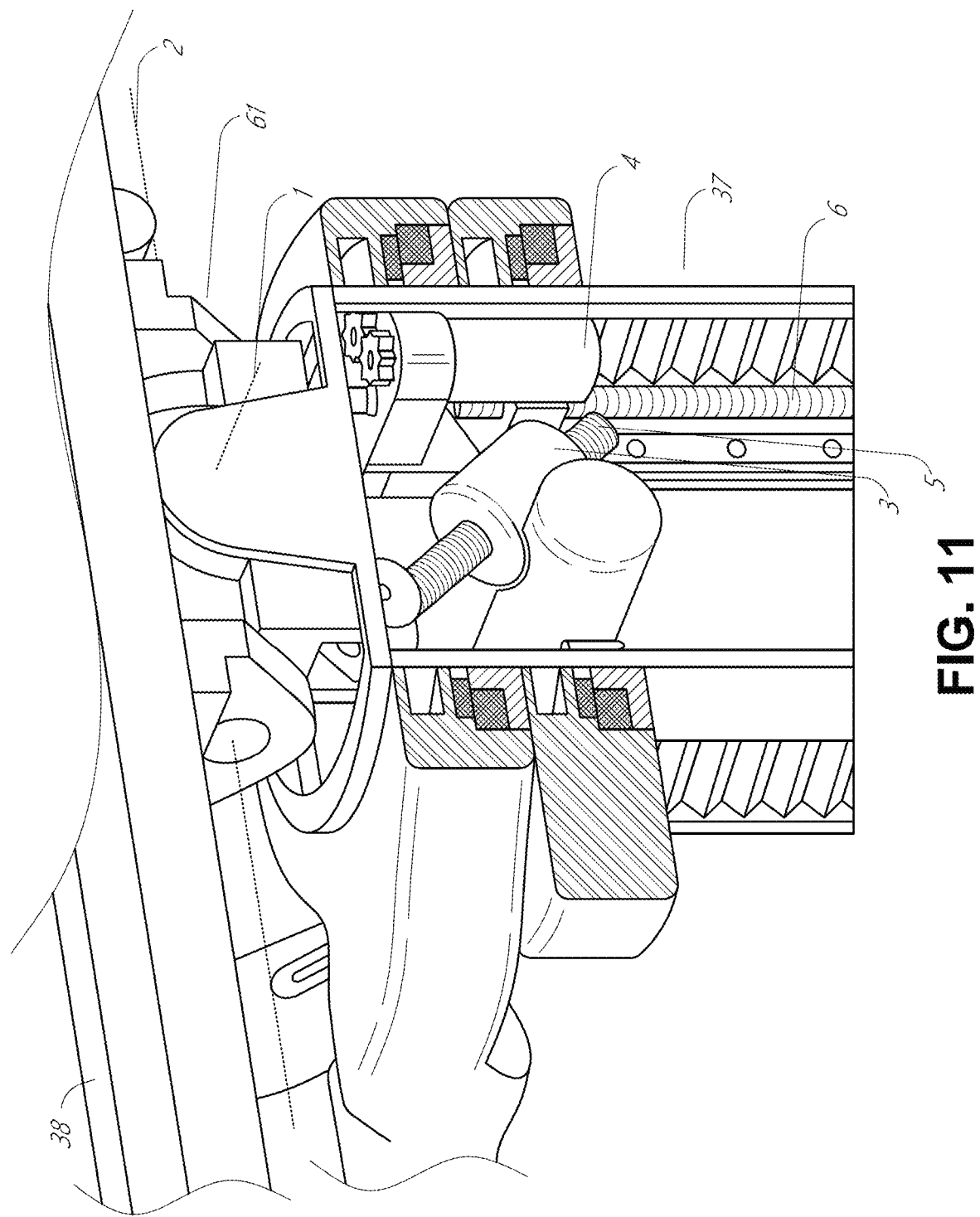
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
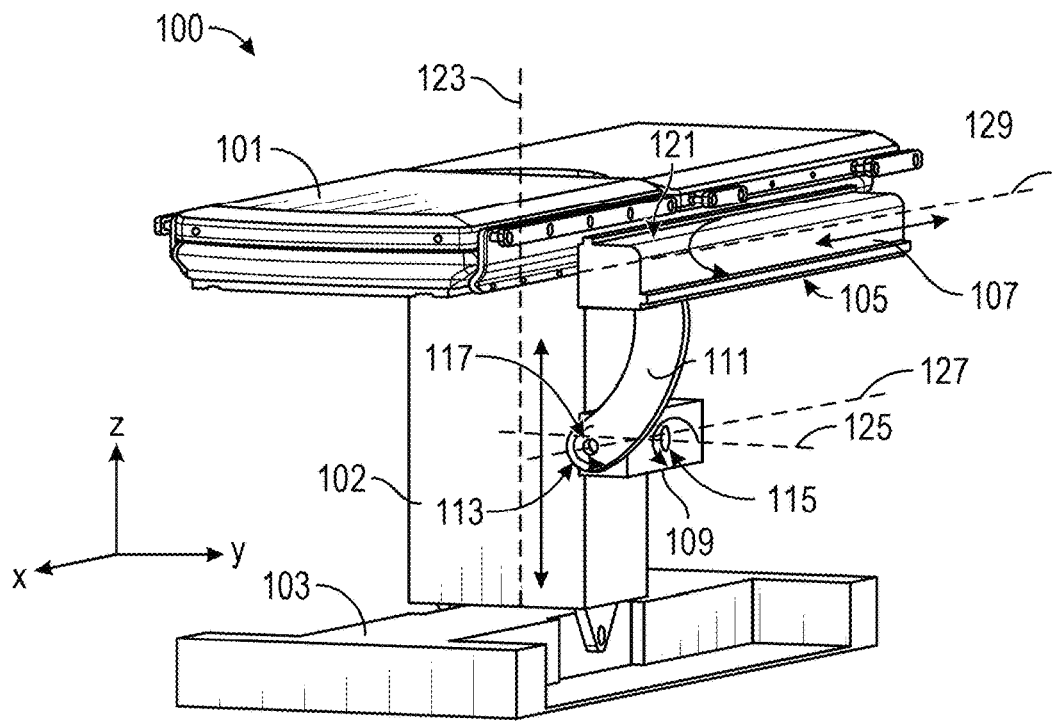
FIG. 12 illustrates an alternative embodiment of a table-based robotic system.
Figure 13:
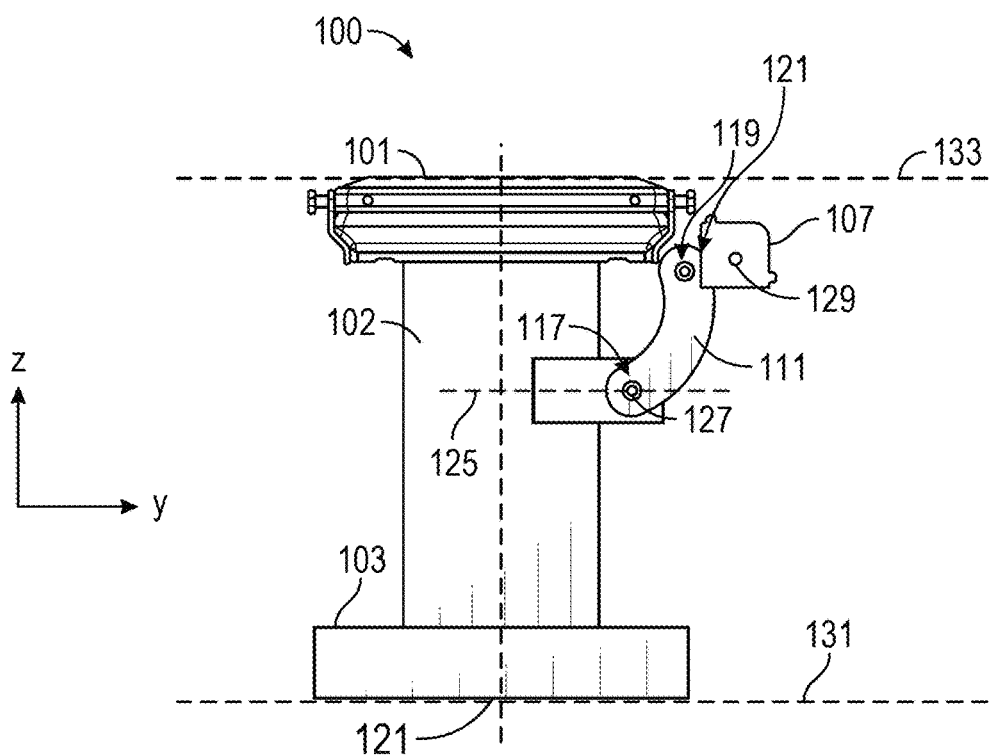
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105.

A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
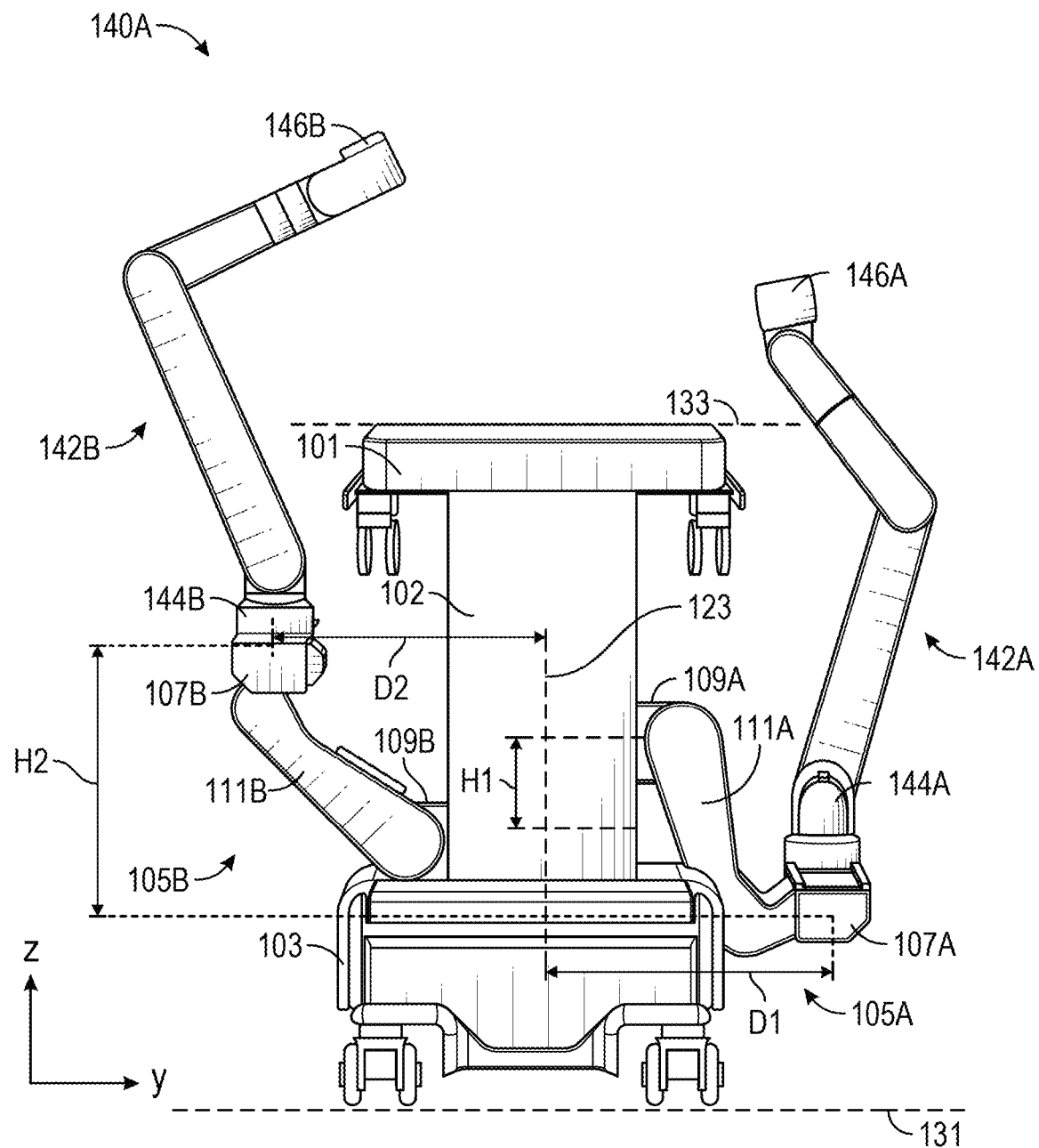
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
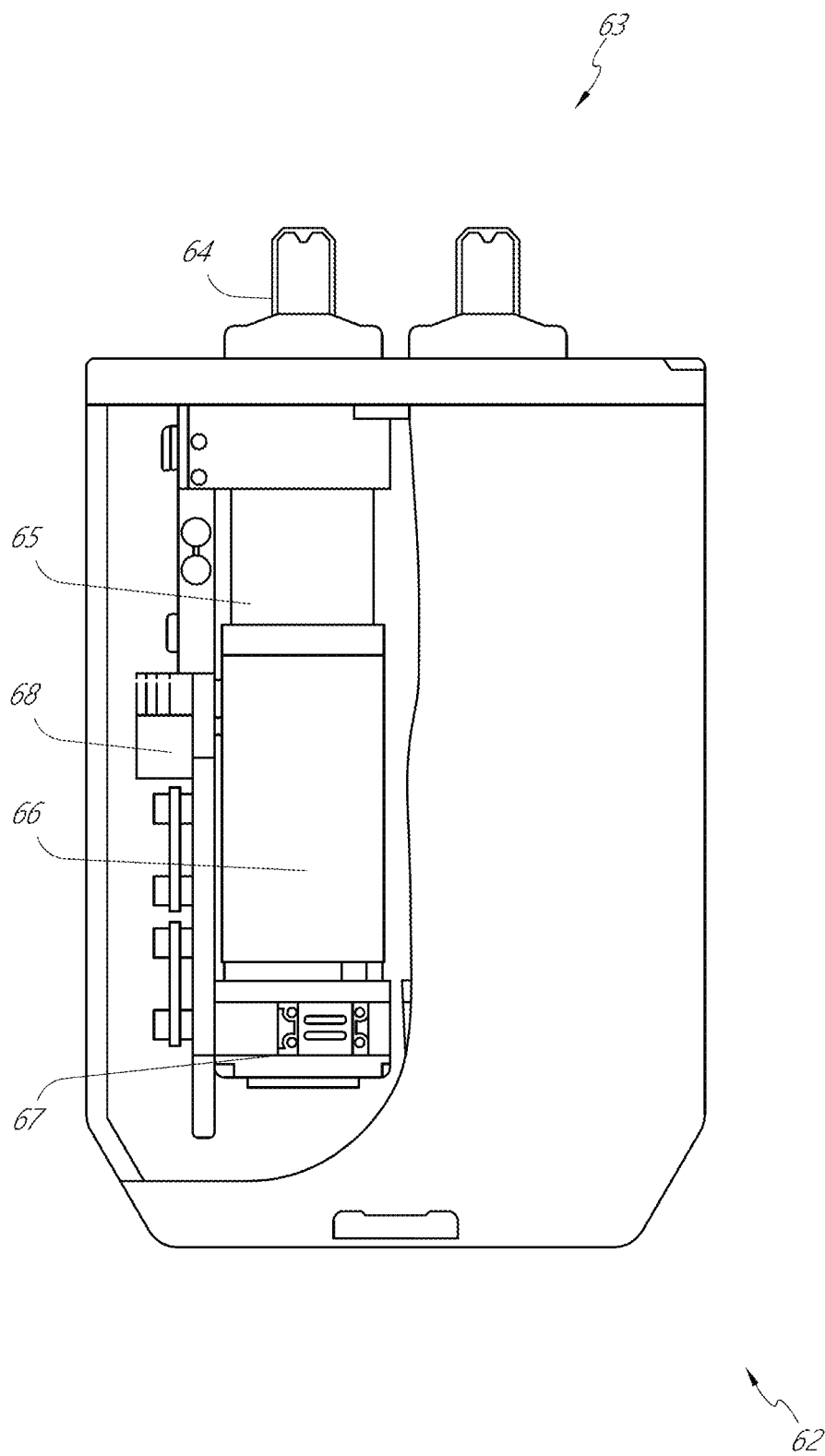
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
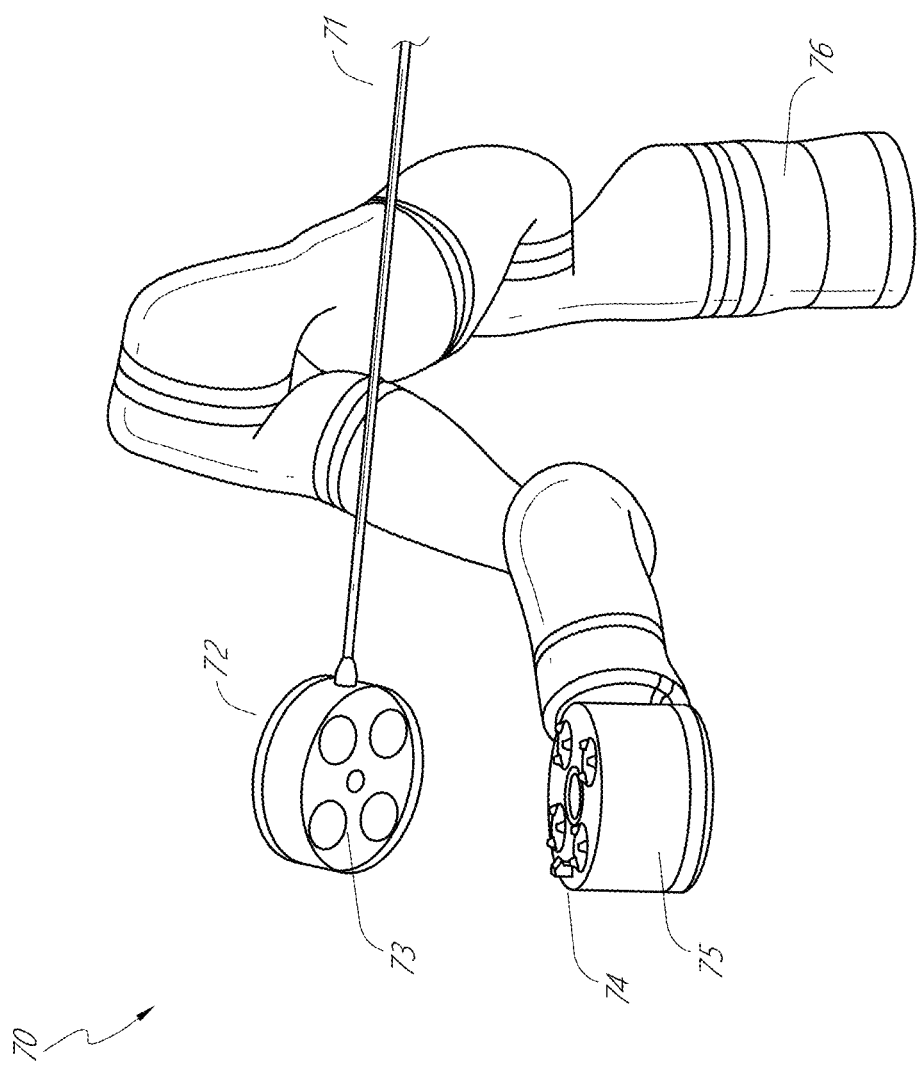
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
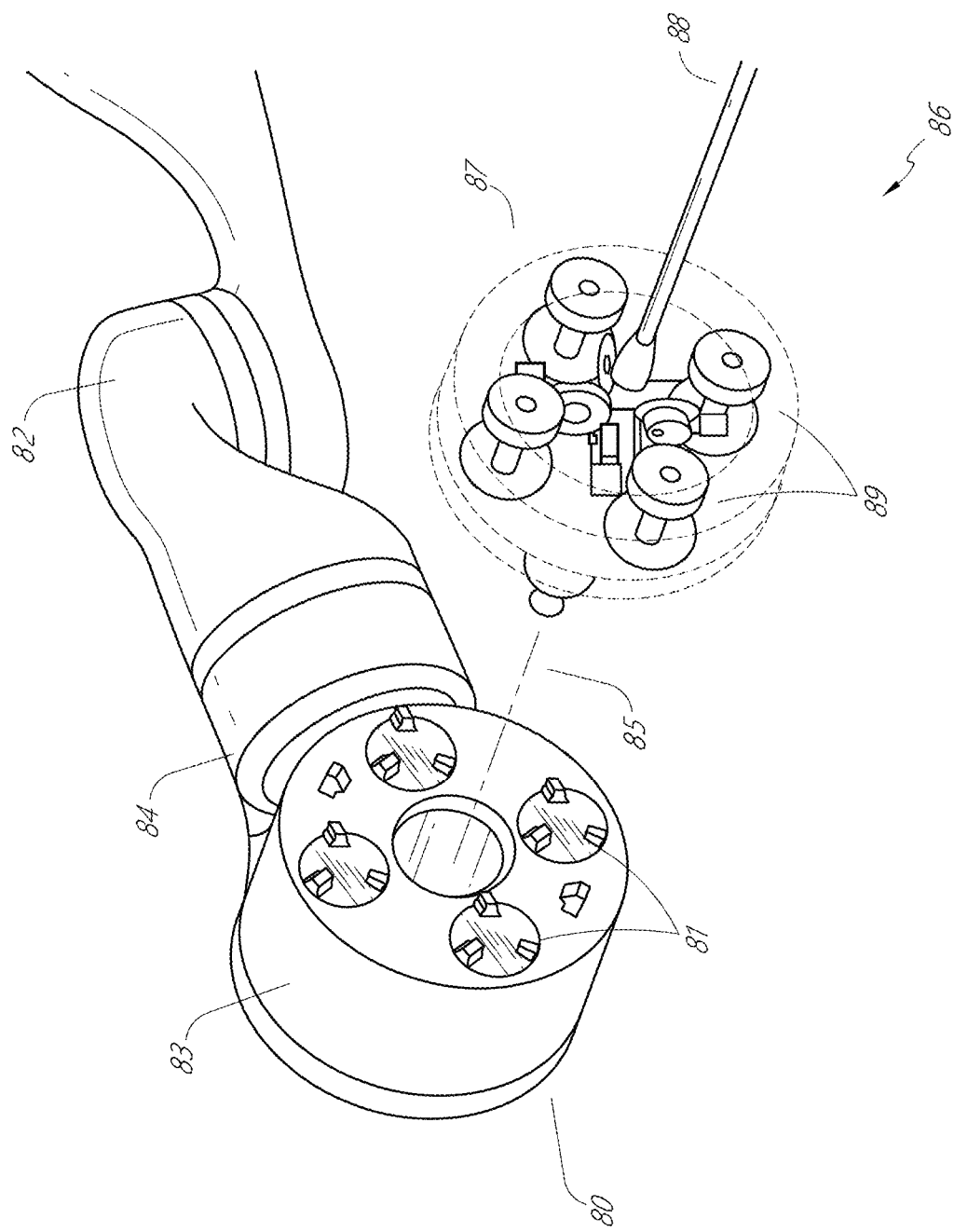
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
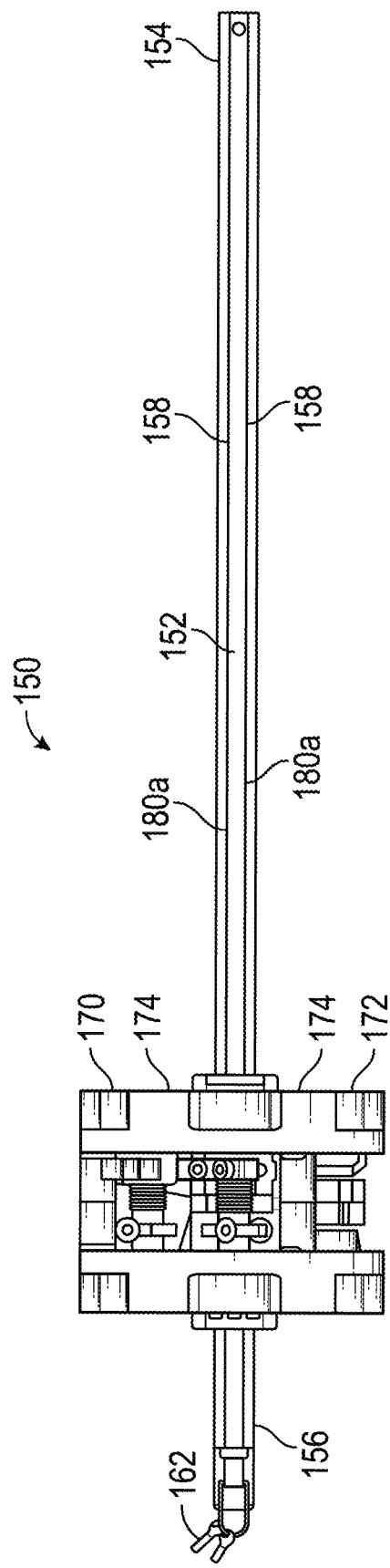
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
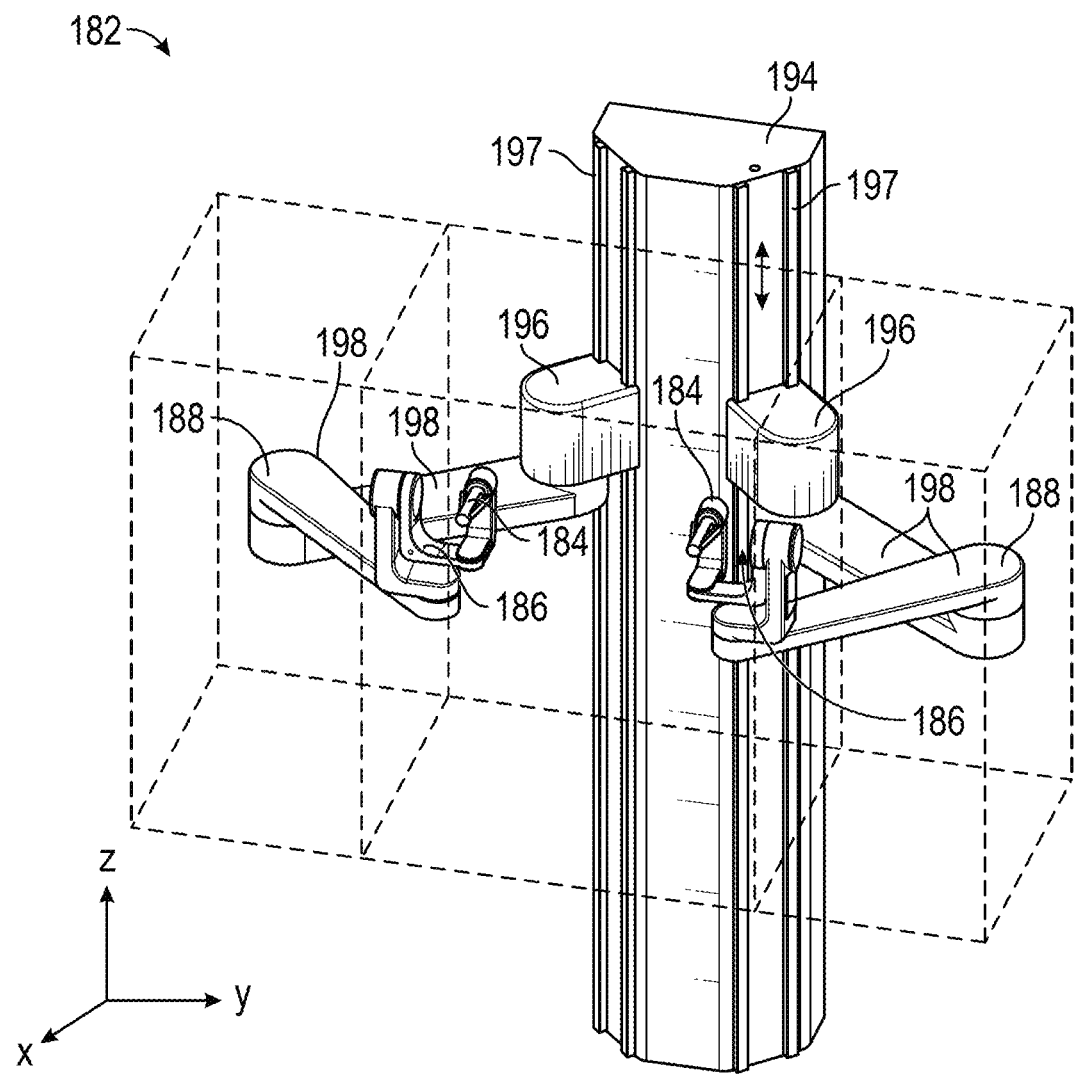
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
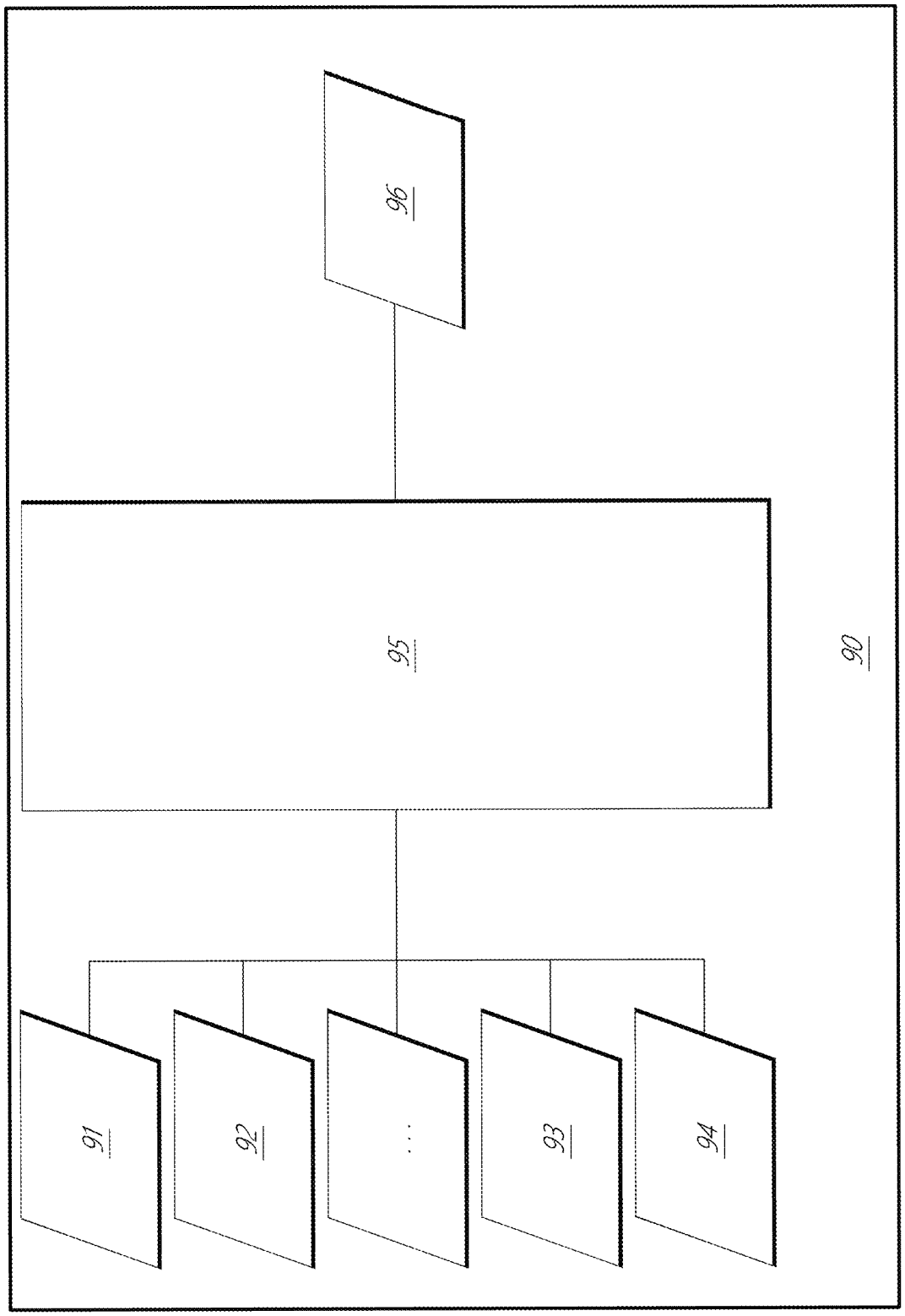
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Robotic Systems and Methods for Concomitant Endoscopic AND Percutaneous Medical Procedures.

Embodiments of the disclosure relate to robotic systems and methods for concomitant endoscopic and percutaneous medical procedures, such as endoscopically-assisted percutaneous (or laparposic) medical procedures and laparoscopically-assisted endoscopic procedures. The systems and methods can be embodied in or employed using robotically-enabled medical systems, such as those described above with reference to FIGS. 1-20 and those described in further detail below.

Many medical procedures involve guiding a medical instrument to a target location within a treatment region of a patient. In some instances, these medical procedures can involve percutaneously guiding the medical instrument through an opening (such as a percutaneous access port) to the target region. Because the target location is often internal, it can be difficult to accurately guide the medical instrument to the target location. Commonly, physicians, and in particular, highly trained radiologists, rely on live fluoroscopic images to guide the medical instrument to the target location. Still, such procedures are difficult. The radiologist must derive a three-dimensional path to the target location from two-dimensional fluoroscopic images, often leading to imprecise guidance and placement of the medical instrument. Further, use of fluoroscopy undesirably exposes the patient and medical staff to radiation for a prolonged period of time.

Percutaneous nephrolithotomy (PCNL), for example, is a medical procedure that involves gaining percutaneous access to a kidney for removal of kidney stones. Commonly, PCNL is performed in two steps. First, a radiologist percutaneously guides an access sheath into the kidney to gain access to the treatment region. The radiologist relies on two-dimensional fluoroscopic images to guide and place the access sheath. Second, with the access sheath in place, a urologist then accesses the treatment region through the access sheath to remove the kidney stone. The common need for a radiologist to perform the first part of the procedure adds cost, complication, and operation scheduling time delay to a procedure that would ideally need only the urologist and their staff to perform. Further, because the radiologist is not trained in urology, the radiologist often places the access sheath in a suboptimal position. However, the urologist must rely on the radiologist to place the access sheath because the urologist is not trained in radiology and thus cannot guide the access sheath himself. Because the radiologist relies on fluoroscopic imaging techniques, another disadvantage of PCNL is the radiation exposure mentioned above.

The methods and systems for concomitant endoscopic and percutaneous medical procedures described in this application can provide improved guidance and placement of percutaneous and/or endoscopic medical instruments. As will be described in greater detail with reference to the following illustrated examples, the methods and systems can be advantageously employed to define rendezvous points for medical instruments within a treatment region and/or to define boundaries within the treatment region for use during the procedure.

Figure 21B:
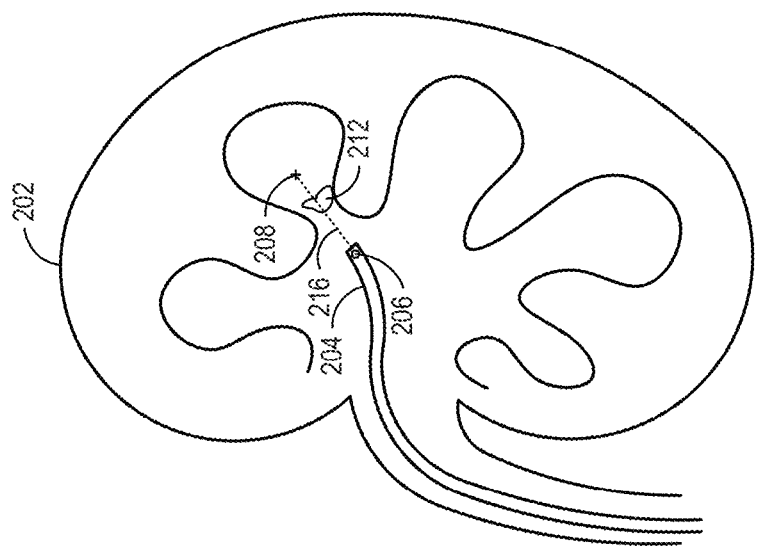
FIGS. 21A-21D illustrate various steps in an embodiment of an endoscopically-assisted percutaneous medical procedure in a kidney.
Figure 21A:
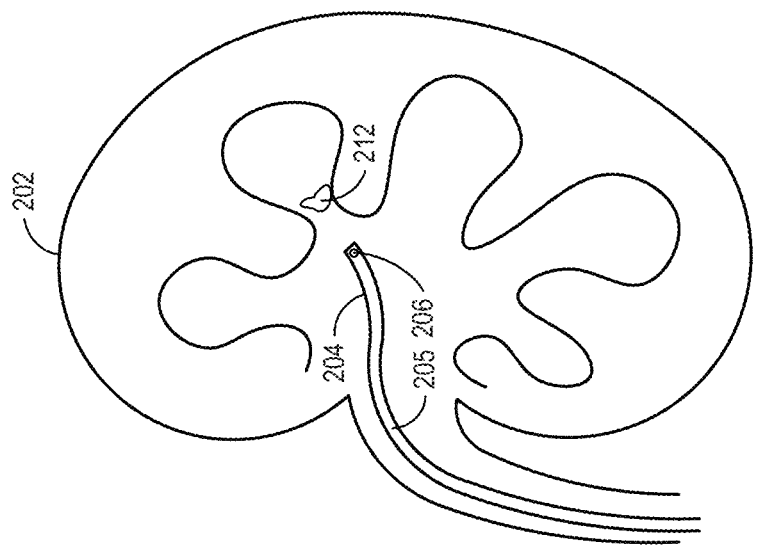
Figure 21D:
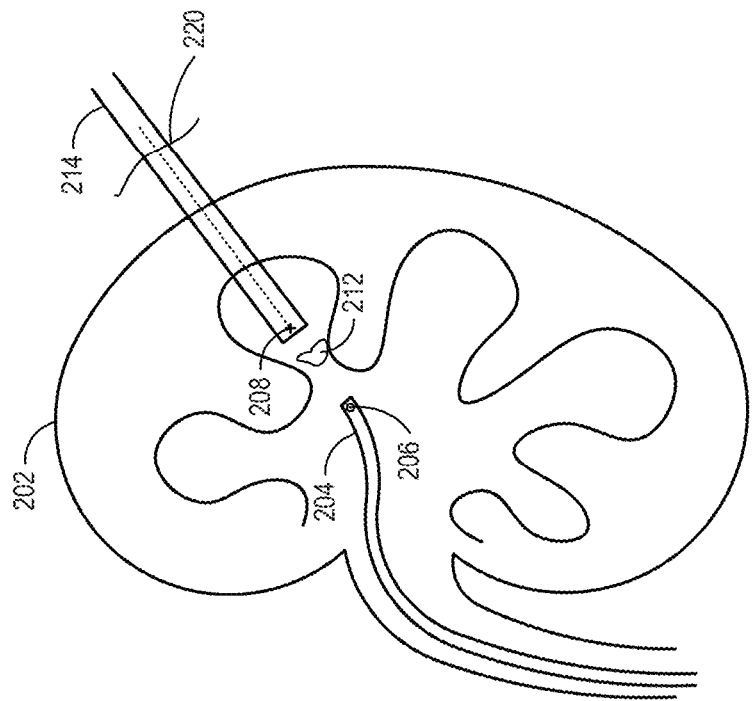
Figure 21C:
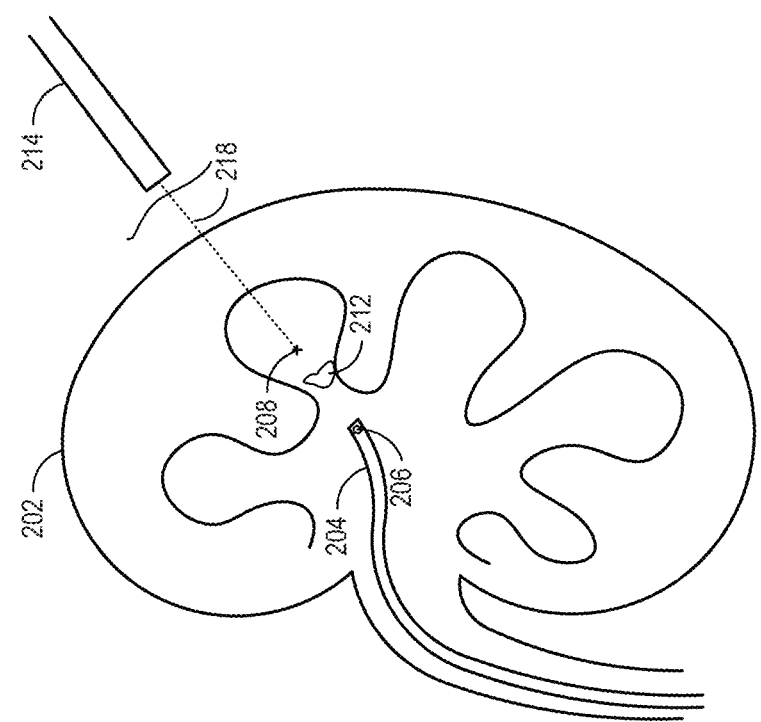

FIGS. 21A-21D illustrate various steps in an embodiment of an endoscopically-assisted percutaneous medical procedure in a kidney 202. In the illustrated example, the medical procedure is an endoscopically-assisted percutaneous nephrolithotomy (PCNL) procedure for removing a kidney stone 212, although the principles illustrated by the example are applicable to other types of medical procedures, all of which are intended to be within the scope of this disclosure. As will be described in detail below, in the illustrated example, a first medical instrument 204 is inserted into the kidney 202 through a natural orifice in the patient (FIG. 21A). The first medical instrument 204 includes a position sensor 206. A target location 208 for guiding percutaneous insertion of a second medical instrument 214 is determined with reference to the position sensor 206 (FIG. 21B). The target location 208 can be distanced from the position sensor 206 as shown. In some embodiments, the target location 208 can be a location (such as a point in space) or a trajectory (such as a line in space). In some embodiments, the target location 208 can be displayed as either a point or line on a graphical user interface. The second medical instrument 214 is aligned with the target location 208 (FIG. 21C). Finally, the second medical instrument 214 is percutaneously inserted toward the target location 208 (FIG. 21D). In this position, PCNL can be performed through the second medical instrument 214. In some embodiments, PCNL can be assisted by the first medical instrument 204.

As will be described in further detail below, the endoscopically-assisted PCNL procedure illustrated in FIGS. 21A-21D can provide several advantages. For example, the procedure can allow for increased accuracy in percutaneous placement of the second medical instrument 214 because insertion of the second medical instrument 214 can be guided toward the target location 208. Also, in some embodiments, the procedure allows for guidance of the second medical instrument 214 without requiring fluoroscopic visualization. This can advantageously reduce or eliminate radiation exposure to the patient and medical personnel during the procedure. This can also simplify the procedure as it may allow the procedure to be performed wholly by a urologist, rather than by both a radiologist and urologist. Further, in some embodiments, because the target location 208 can be determined with reference to the position sensor 206, but at positions that are distanced from the position sensor 206, the target location 208 can be determined at positions that cannot be directly accessed by the first medical instrument 204. As an example, in some embodiments, the procedures may enable placement of an access port in a single attempt. In contrast, other techniques (such a fluoroscopy guided techniques) sometimes require the physician to retract and replace the tool multiple times until the correct location is finally achieved. These and other advantages will be described in greater detail below with more specific reference to the figures.

As mentioned above, FIGS. 21A-21D illustrate various steps in an endoscopically-assisted percutaneous nephrolithotomy (PCNL) procedure for removing a kidney stone 212. As shown in FIG. 21A, in the illustrated example, the kidney stone 212 is positioned at the entrance to a calyx. In some instances, a urologist may desire to insert an access sheath into the kidney 202 within the calyx and behind the kidney stone 212. PCNL can then be performed through the access sheath to break up and remove the kidney stone 212. Accurate placement of the access sheath can be important for maximizing the efficacy of the procedure and minimizing stress and impact on the patient.

In the illustrated example, to accurately place the access sheath, first, the first medical instrument 204 can be guided into the kidney 202. In some embodiments, the first medical instrument 204 is inserted into the patient through a natural orifice. For example, the first medical instrument 204 can be inserted through the urethra, bladder, and ureter into the kidney 202. In some embodiments or in other procedures, other natural patient orifices can be used. In some embodiments, the first medical instrument 204 can be inserted percutaneously.

The first medical instrument 204 can be an endoscope. In some embodiments, the first medical instrument 204 can be robotically controlled. For example, the first medical instrument can by any of the robotically-controllable medical instruments described above with reference to FIGS. 1-20. In some embodiments, the first medical instrument 204 can be manually controlled. As illustrated in FIG. 21A, the first medical instrument 204 can include an elongated shaft 205. The elongated shaft 205 can be articulable and controllable such that the first medical instrument 204 can be navigated through the patient's anatomy into the kidney 202. Several embodiments for such medical instruments are described above with reference to FIGS. 16-18. The medical instrument 204 can also include, in some embodiments, various other features such as optical systems (such as cameras), which can allow an operator to visualize the treatment region from the point of view of the first medical instrument 204, and working channels, which can allow for delivery of additional medical tools or instruments through the elongated shaft 205 to the treatment region. In some embodiments, the working channels may be used to deliver fluid or to aspirate fluid or debris.

Also illustrated in FIG. 21A, the first medical instrument 204 can include a position sensor 206. In the illustrated embodiment, the position sensor 206 is positioned at or near the distal end of the elongated shaft 205 of the first medical instrument 204. In other embodiments, the position sensor 206 can be positioned in other locations on the elongated shaft 205. In some embodiments, the first medical instrument 204 includes a plurality of position sensors 206. The position sensor 206 is configured to provide an output from which the location or position of the position sensor 206 (and the first medical instrument 204) can be determined. In some embodiments, the position sensor 206 comprises an electromagnetic (EM) sensor configured to produce a detectable signal within an EM field from which the position of the EM sensor within the EM field can be determined. In some embodiments, the position sensor 206 comprises a shape sensing fiber from which the pose or shape of the elongated shaft 205 can be determined and used to determine the position of the medical instrument 204. In other embodiments, other types of position sensors can be used.

As shown in FIG. 21A, during the procedure, the first medical instrument 204 is guided into the kidney 202. In some embodiments, guidance of the first medical instrument 204 is facilitated by a navigation or localization system, such as localization system 90 described above. The operator may visualize the kidney stone 212 using the optical system on the first medical instrument 204.

As shown in FIG. 21B, with the first medical instrument 204 positioned within the kidney 202, the operator (or the system) can determine a target location 208. The target location 208 may represent a location at which it is desired that the second medical instrument 214 (see FIGS. 21C and 21D) be placed. As will be described below with reference to FIGS. 21C and 21D, the target location 208 can provide a beacon that is used for guiding insertion of the second medical instrument 214. For example, the second medical instrument 214 can be guided so as to rendezvous with the target location 208.

In some embodiments, the target location 208 can be determined with reference to the position sensor 206 but at a position that is distanced from the position sensor 206. That is, the target location 208 need not be coincident with the position sensor 206 (or any other point on the first medical instrument 204).

For example, in some embodiments, the output of the position sensor 206 can be registered to a preoperative model of the kidney 202. Registration can involve, for example, using the position sensor 206 to map the path of the first medical instrument 204 through the anatomy, and matching the mapped path to the preoperative model. As another example, registration can involve navigating the medical instrument 204 to one or more anatomical landmarks, and using the output of the position sensor 206 at the one or more anatomical landmarks to register the preoperative model to the output of the position sensor 206. Additional detail on registration is provided above with reference to localization system 90 and FIG. 20. Once the preoperative model is registered, the operator (or the system) may, in some embodiments, determine the target location 208 by selecting it within the preoperative model. For example, the preoperative model can be displayed to the operator, and the operator can select a location from within the preoperative model to be the target location 208. As noted above, the target location 208 can be distanced from the position sensor 206. In some embodiments, using the preoperative model and data from the position sensor 206, a distance and direction between the location of the position sensor 206 and the chosen target location 208 can be determined by the system. For example, the location of the position sensor 206 can be represented as an x, y, z coordinate, the target location 208 can be represented by an x', y', z' coordinate, and a distance and direction between the x, y, z coordinate and x', y', z' coordinate can be determined.

In another example, the target location 208 can be determined with reference to intraoperative medical imaging, such as one or more fluoroscopic images. For example, an operator can select a location on a fluoroscopic image as the target location 208. Again, the target location 208 can be distanced from the position sensor 206. In some embodiments, the output of the position sensor can be registered to the fluoroscopic image such that a relationship between the target location 208 and the position sensor 206 can be determined. As an example, the position sensor 206 can be an electromagnetic (EM) sensor. The EM base frame can be registered to a pre-operative CT image by moving the instrument including the EM sensor back and force in a known bronchial branch. This can generate corresponding point pairs in both coordinate frames (i.e., the EM base frame and the fluoroscopic frame). With the corresponding point pairs, algorithms can be used to determine a transform between the coordinate frames. This process is often or generally referred to as registration. Once the transform is determined, the position sensor 206 can be shown in the fluoroscopic image frame, and the relationship between the target location 208 defined in image frame and the sensor can be determined.

In some embodiments, the target location 208 is selected along an axis 216 that extends outwardly from the distal tip of the elongated shaft 205 of the first medical instrument 204 (as shown, for example, in FIG. 21B). For example, the target location 208 can be a projection of the location of the position sensor 206 along the axis 216. In other embodiments, the target location 208 need not lie on the axis 216. That is, the target location 208 can be a projection of the position sensor 206 in any direction.

Selecting a target location 208 that is distanced from the position sensor 206 can advantageously allow the use of target locations 208 that are not directly accessible by the first medical instrument 204. For example, in the illustrated example, the kidney stone 212 is positioned in an entrance of a calyx. In this position, the kidney stone 212 may prevent the medical instrument 204 from navigating into the calyx. Advantageously, the target location 208 can be projected into the calyx, even if the first medical instrument 204 is not physically able to navigate into the calyx. Similarly, the target location 208 can be determined at positions that cannot even be visualized with the first medical instrument 204. In the illustrated example, the kidney stone 212 may even block visual access to the calyx. Regardless, the target location 208 can be advantageously projected into the calyx.

As shown in FIG. 21C, the target location 208 can be used as a beacon for aligning the second medical instrument 214. In the illustrated embodiment, the second medical instrument 214 can be a percutaneous access sheath. In other embodiments, the second medical instrument can be other types of medical instruments, such as endoscopic or laparoscopic tools, for example. In the illustrated embodiment, the second medical instrument 214 can be manipulated until an axis 218 of the second medical instrument 214 is aligned with the target location 208.

In some embodiments, the second medical instrument 214 can be positioned on an instrument positioning device, such as a robotic arm. The instrument positioning device can be robotically controlled to automatically align the second medical instrument 214 with the target location. For example, the second medical instrument 214 can be robotically aligned with the target location 208 based on the position of the instrument positioning device or an output of a position sensor on the second medical instrument 214.

In some embodiments, the second medical instrument 214 can be manually aligned with the target location 208. In such embodiments, the second medical instrument 214 can include one or more position sensors for determining the position and orientation of the second medical instrument 214. An example process for aligning the second medical instrument 214 will be described in greater detail below with reference to FIGS. 22A and 22B.

As shown in FIG. 21D, with the second medical instrument 214 aligned with the target location 208, the second medical instrument 214 can be guided or inserted so as to rendezvous with the target location 208. In the illustrated embodiment, the second medical instrument 214 is percutaneously inserted into the kidney 202, for example, through a percutaneous opening 220. In some embodiments, the percutaneous opening 220 is created by the second medical instrument 214. In some embodiments, the percutaneous opening 220 is created separately, for example, by a separate medical tool, prior to insertion of the second medical instrument 214.

Figure 23A:
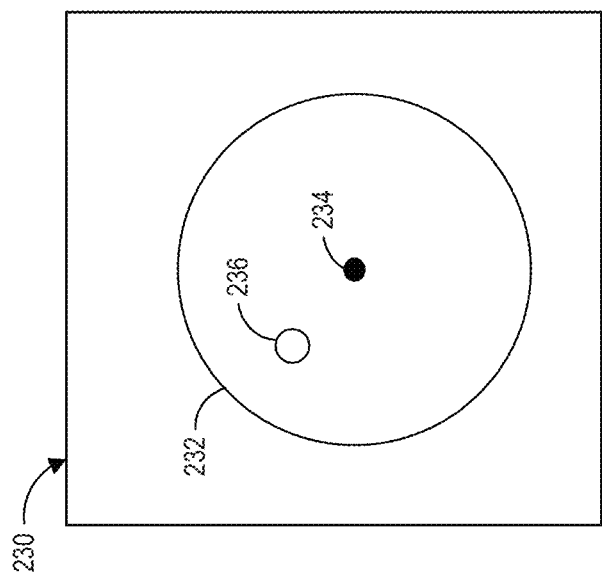
FIGS. 23A and 23B illustrate an example alignment interface for assisting with the fine alignment step of FIG. 22B, according to one embodiment.
Figure 23B:
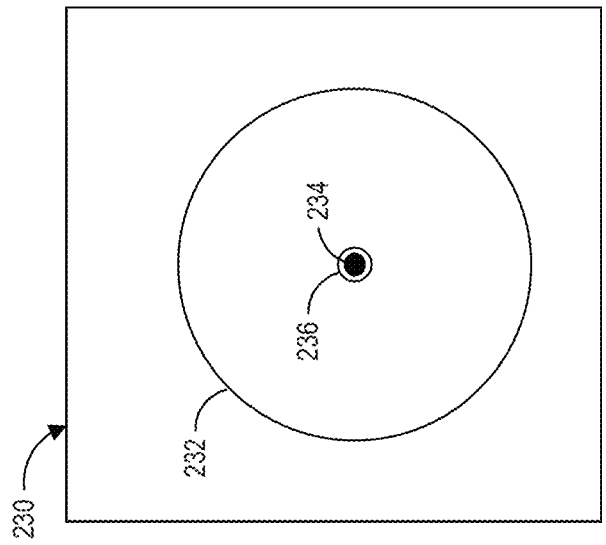

Insertion of the second medical instrument 214 can occur in a variety of ways. For example, insertion can be manual or robotic. In some manual embodiments, a physician manually inserts the second medical instrument 214. The physician can guide the second medical instrument 214 toward the target location 208. In some embodiments, an alignment interface can be provided that aids the physician in maintaining alignment of the medical instrument 214 with the target location 208 during insertion. An example alignment interface is shown in FIGS. 23A and 23B described below.

In some embodiments, the insertion of the second medical instrument 214 can be robotic. The second medical instrument 214 can be positioned on an instrument positioning device, such as a robotic arm. In some embodiments, the instrument positioning device maintains alignment during insertion while the physician inserts the second medical instrument 214 by physically handling (e.g., pushing) the second medical instrument 214 (or the instrument positioning device). In these embodiments, alignment can be maintained robotically, while the actual insertion of the second medical instrument 214 is performed manually. For example, the physician can hold a handle on the second medical instrument 214 or the instrument positioning device to push the second medical instrument 214 into the patient. The instrument positioning device can limit or restrict motion of the second medical instrument 214 to motions along the axis of insertion. For example, the instrument positioning device can limit or prevent motions that would cause the second medical instrument 214 to move out of alignment with the target location 208. In some embodiments, motion is limited to only along the insertion axis. In some embodiments, motion is limited to a range around the insertion axis. For example, motion can be limited to within a cone-shaped or cylindrical-shaped boundary around the insertion axis. In some embodiments, the motion is limited by haptic boundaries. Haptic boundaries can physically limit motion outside of the allowed range or provide tactile feedback to the physician that the motion is off track.

In some embodiments, the physician commands insertion using a controller, and both alignment and insertion are performed robotically. As in the previous example, the robotic system can limit or prevent motion such that the second medical instrument 214 remains in alignment with the target location 208.

In some embodiments, during alignment (FIG. 21C) and insertion (FIG. 21D) of the second medical instrument 214, the first medical instrument 204 remains in the treatment region (e.g., in the kidney 202). The output signal of the position sensor 206 can be used to track patient motion during the procedure. Patient motion may comprise respiration. For example, as the patient breathes, the kidney 202 may move slightly. This motion can be tracked using the position sensor 206. This patient motion can then be compensated for during alignment and insertion of the second medical instrument 214 such that accuracy of the rendezvous of the second medical instrument 214 with the target location 208 is increased. In some embodiments, to accurately track and compensate for patient motion, the first medical instrument 204 should remain positioned during alignment and insertion such that the position sensor 206 remains in proximity to the target location 208.

In some embodiments, insertion of the second medical instrument 214 stops when the second medical instrument 214 reaches the target location 208 as shown in FIG. 21D. With the second medical instrument 214 in the position illustrated in FIG. 21D, the physician can perform PCNL to remove the kidney stone 212.

As mentioned above, FIGS. 22A and 22B illustrate various steps in an embodiment of an alignment process that can be used for aligning the second medical instrument 214 with the target location 208. FIG. 22A illustrates an example of a gross alignment step during which a distal end of the second medical instrument 214 is brought into proximity with the target location 208, and FIG. 22B illustrates an example of a fine alignment step during which an axis 218 of the second medical instrument 214 is aligned with the target location 208. In some embodiments, the alignment process described with respect to FIGS. 22A and 22B is used for manual alignment and insertion of the second medical instrument 214. In some embodiments, robotic alignment and insertion can employ a similar process.

As shown in FIG. 22A, the alignment process can involve, first, grossly positioning the second medical instrument 214 with respect to the target location 208. As illustrated, this can involve moving the second medical instrument 214 along or near the surface of the patient's skin 203 until the distal tip of the second medical instrument 214 is positioned within a zone 226 (represented visually by the area between two dashed lines) that is in proximity to the target location 208. The position of the zone 226 can be determined to be an anatomical region in proximity to the target location 208 or an anatomical region where it is desirable to make the percutaneous insertion. The position of the distal tip of the second medical instrument 214 can be tracked using a position sensor 222, which can be similar to any of the position sensors previously described. As illustrated, the physician can move the second medical instrument 214 back and forth, for example, in the directions of the arrows 224, until the position sensor 222 is within the zone 226. The system may provide an alert to the physician when the position sensor 222 is within the zone 226. The alert may be, for example, audible or visual. As illustrated in FIG. 22A, during this step, the axis 218 of the second medical instrument 214 need not necessarily be aligned with the target location 208. Rather, this step may focus on merely bringing the second medical instrument 214 into the zone 226 in proximity to the target location 208.

Once the second medical instrument 214 is positioned within the zone 226 (to provide a gross alignment), the physician may then focus on aligning the axis 218 of the second medical instrument 214 with the target location 208. An example of this step is illustrated in FIG. 22B. During this step, the physician can maintain the distal tip of the second medical instrument 214 in position, and rotate or pivot the second medical instrument 214 about that point until the axis 218 is aligned with the target location 208. For example, the physician may rotate or pivot the second medical instrument 214 in the directions of the arrows 228 until the axis 218 is aligned with the target location 208. This may provide a fine alignment for the second medical instrument 214 and the target location 208.

An alignment interface can be used to facilitate alignment of the axis 218 with the target location 208. In some embodiments, the alignment interface is a graphical user interface that provides a visual representation of alignment. An example of such an alignment interface is shown in FIGS. 23A and 23B, described below. In other embodiments, the alignment interface may user other methods for indicating alignment, such as audible cues, for example.

FIGS. 23A and 23B illustrate an example alignment interface 230 for assisting with the fine alignment step of FIG. 22B, according to one embodiment. In FIGS. 23A and 23B, the upper portion of the figures show an example of the alignment interface 230, and the lower portions of the figures show corresponding examples of how the second medical instrument 214 and the target location 208 are aligned.

As shown in FIG. 23A, the alignment interface 230 can comprise a graphical or visual representation of alignment. In the illustrated embodiment, the alignment interface 230 comprises an outer circle 232, a target indicator 234, and an instrument indicator 236. The target indicator 234 can represent the position of the target location 208. In some embodiments, the target indicator 234 remains in the center of the circle 232. The instrument indicator 236 can represent the current alignment of the second medical instrument 214 relative to the target location 208. As the second medical instrument 214 moves, the instrument indicator 236 moves around the circle 232 as the relative alignment between the second medical instrument 214 and the target location 208 changes.

In some embodiments, the alignment interface 230 is representative of a view of alignment looking down the shaft of the second medical instrument 214. For example, as illustrated in FIG. 23A, the instrument indicator 236 is positioned above and to the left of the target indicator 234. This can indicate that the second medical instrument 214 is misaligned in a direction up and to the left of the target location 208. The physician can interpret the alignment interface 230 to know that the second medical instrument 214 should be pivoted down and to the right so as to align with the target location 208.

FIG. 23B illustrates the alignment interface 230 when the second medical instrument 214 is aligned with the target location 208. As shown, when aligned, the instrument indicator 236 can overlap the target indicator 234. A physician may first use the alignment interface 230 to properly align the second medical instrument 214 with the target location 208. The physician may then continue to use the alignment interface 230 during insertion to maintain alignment while inserting. As the physician inserts the second medical instrument 214, the physician may focus on maintaining alignment by keeping the instrument indicator 236 overlapped with the target indicator 234. The user can then continue to insert the second medical instrument 214 until the desired depth is reached.

Figure 24:
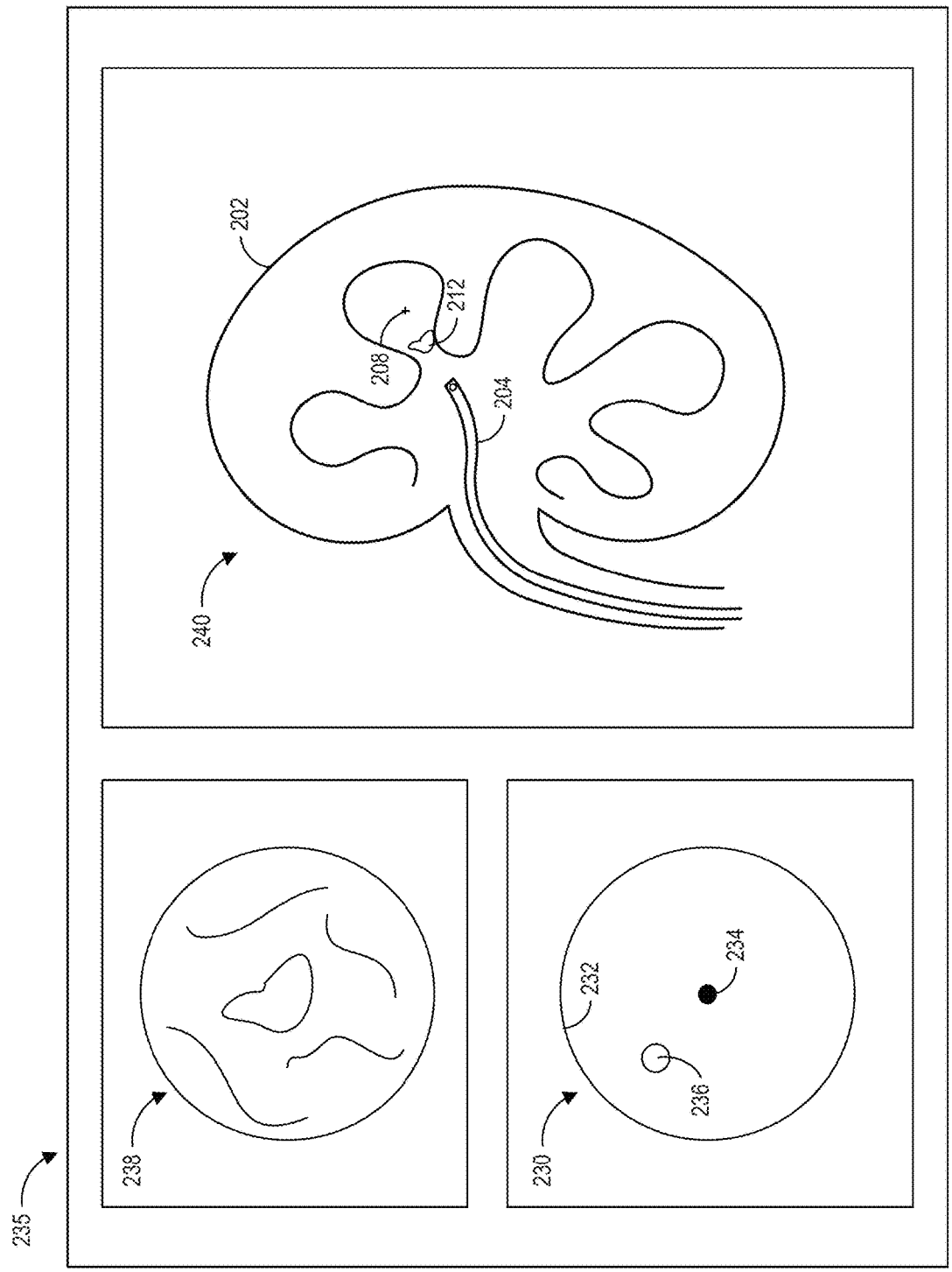
FIG. 24 illustrates an example user interface that includes the alignment interface of FIGS. 23A and 23B.

The alignment interface 230 can be displayed to the user, for example, as part of a graphical user interface for the robotic system. FIG. 24 illustrates an example of such a graphical user interface 235 that includes the alignment interface 230. The graphical user interface 235 can include various screen portions for displaying information to the user. For example, in the illustrated embodiment, the graphical user interface 235 includes the alignment indictor 230, an endoscope view 238, and a model or fluoroscopic view 240. The endoscopic view 238 can display a live view from the optical system on the first medical instrument 204. The model or fluoroscopic view 240 can display the preoperative view of a live fluoroscopic view of the treatment region. In some embodiments the target location 208 can be displayed on the model or fluoroscopic view 240. In some embodiments, the physician can use the model or fluoroscopic view 240 to select the target location 208. The graphical user interface 235 illustrated in FIG. 24 is provided by way of example only. Other graphical user interfaces 235 can be used showing more, less, or other types of information than are depicted in FIG. 24.

Figure 25B:
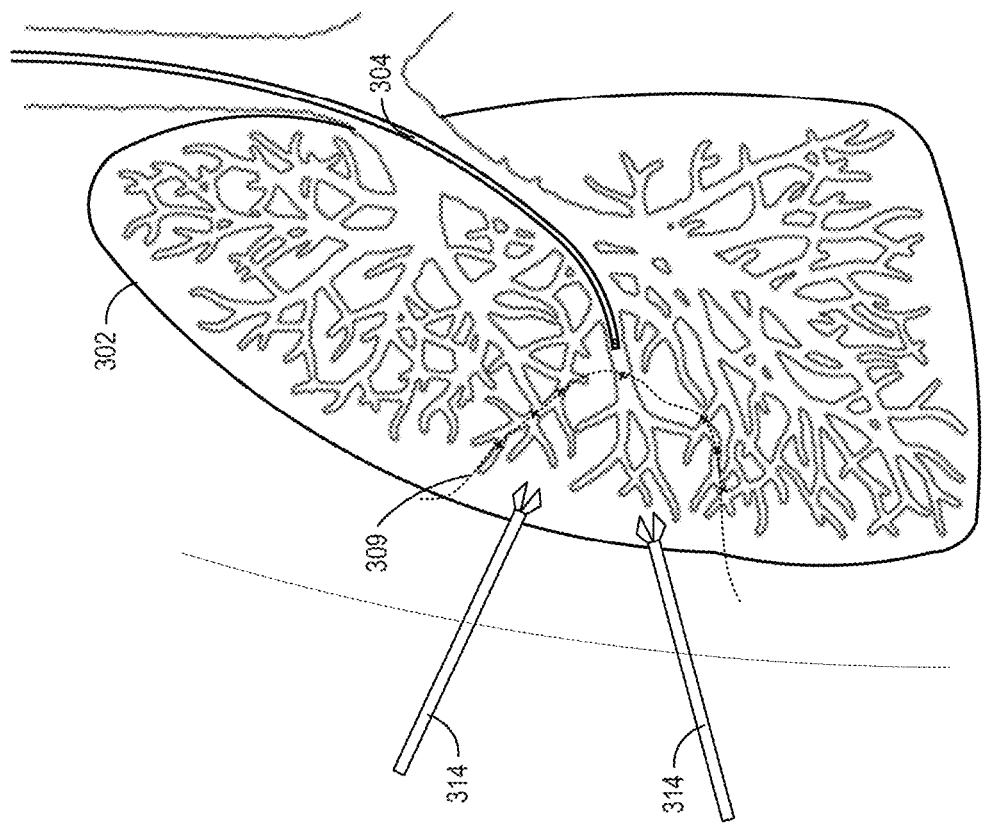
FIGS. 25A and 25B illustrate various steps in another embodiment of an endoscopically-assisted percutaneous medical procedure in a lung.
Figure 25A:
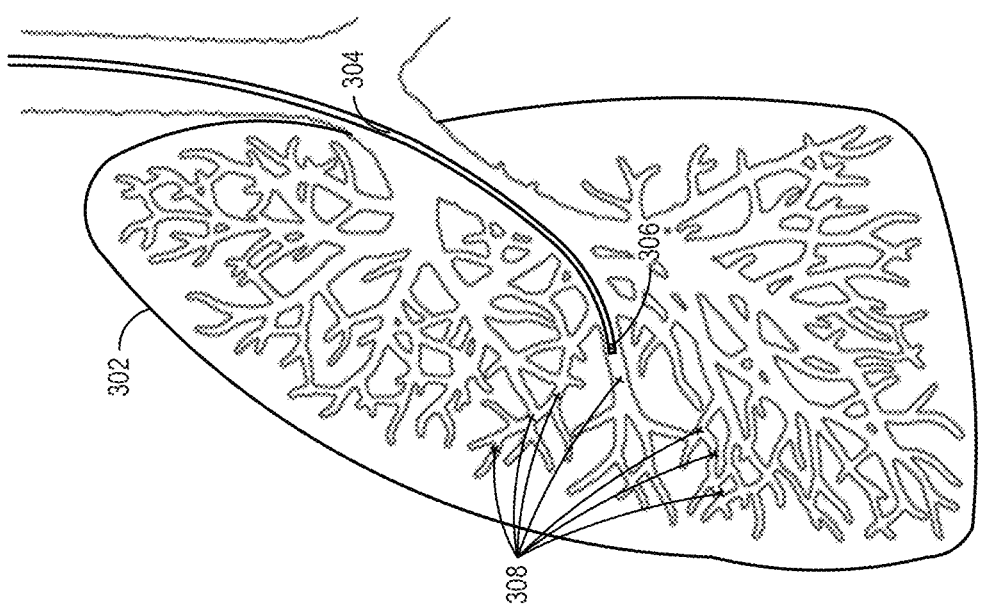

FIGS. 25A and 25B illustrate various steps in another embodiment of an endoscopically-assisted percutaneous medical procedure in a lung 302. In the illustrated example, the medical procedure is an endoscopically-assisted resection procedure for removing a portion of the lung 302, although the principles illustrated by the example are also applicable to other types of medical procedures, all of which are intended to be within the scope of this disclosure. As will be described in detail below, in the illustrated example, a first medical instrument 304 is inserted into the lung 302 through a natural orifice in the patient (FIG. 25A). The first medical instrument 304 includes a position sensor 306. Positions for one or more virtual fiducials 308, for defining a resection boundary, can be determined with reference to the position sensor 306 (FIG. 25A). A boundary 309 can be determined based on the virtual fiducials 308 (FIG. 25B). One or more second medical instruments 314 can perform percutaneous resection of a portion of the lung 302 based on the virtual fiducials 308 and boundary 309 (FIG. 25B).

As will be described in further detail below, the endoscopically-assisted resection procedure illustrated in FIGS. 25A and 25B can provide several advantages. For example, the procedure can allow for increased accuracy in defining the boundary 309. Further, in some embodiments, motion of the second medical instruments 314 can be restricted such that the second medical instruments 314 cannot be moved beyond the boundary. This can minimize the total portion of lung 302 that is resected and reduce the likelihood that healthy tissue will be harmed. Also, in some embodiments, the procedure allows for guidance of the second medical instrument 314 without requiring fluoroscopic visualization. Previously, such resection procedures have involved placing physical radio-opaque markers (such as metallic markers) within the lung, and then viewing the markers fluoroscopically during the procedure to visualize the boundary. Alternatively, the lung could be physically marked with dye that can be visualized using a bronchoscope to guide resection. The virtual fiducials 308 and boundary 309 described in this application can, in some embodiments, be viewed with reference to a preoperative model that has been registered to the anatomy, and thus can be viewable without fluoroscopy. These and other advantages will be described in greater detail below with more specific reference to the figures.

FIG. 25A illustrates an example of placing or creating virtual fiducials 308 during the procedure. In the illustrated example, a physician may desire to resect a portion of the lung 302. To guide resection, the physician may place virtual fiducials 308 that can be used to define a boundary around the portion of the lung 302 that will be resected. Resection can then be performed percutaneously based on the boundary. In the illustrated example, to accurately place the virtual fiducials 308, first, the first medical instrument 304 is guided into the lung 302. In some embodiments, the first medical instrument 304 is inserted into the patient through a natural orifice. For example, the first medical instrument 304 can be inserted through the patient's mouth and trachea into the lung 302. In some embodiments or in other procedures, other natural patient orifices can be used. In some embodiments, the first medical instrument 304 can be inserted percutaneously.

The first medical instrument 304 can be an endoscope, such as a bronchoscope. In some embodiments, the first medical instrument 304 can be robotically controlled. For example, the first medical instrument 304 can by any of the robotically-controllable medical instruments described above with reference to FIGS. 1-20. In some embodiments, the first medical instrument 304 can be manually controlled. As illustrated in FIG. 25A, the first medical instrument 304 can include an elongated shaft. The elongated shaft can be articulable and controllable as described previously such that the first medical instrument 304 can be navigated through the patient's airways within the lung 302. The first medical instrument 304 can also include a position sensor 306 as described in the previous example. The position sensor 306 is configured to provide an output signal from which the position of the position sensor 306 can be determined. Guidance of the first medical instrument 304 can be facilitated by a navigation or localization system, such as localization system 90 described above.

As shown in FIG. 25A, with the first medical instrument 304 positioned within the lung 302, the physician (or the system) can determine locations for one or more virtual fiducials 308. The virtual fiducials 308 can be used to mark the boundary of the resection volume similar to how physical fiducials or dye has been used previously. However, the virtual fiducials 308 can be placed virtually, for example, with reference to a preoperative model that has been registered to the anatomy. For example, in some embodiments, the output of the position sensor 306 can be registered to a preoperative model of the lung 302. Registration can be accomplished as described above, for example, by using the position sensor 306 to map the path of the first medical instrument 304 through the anatomy, and matching the mapped path to the preoperative model, or navigating the medical instrument 304 to one or more anatomical landmarks, and using the output of the position sensor 306 at the one or more anatomical landmarks to register the preoperative model to the output of the position sensor 306.

In some embodiments, virtual fiducials 308 are placed by navigating the first medical instrument 304 to a position within the lung 302 at which it is desired to place a virtual fiducial 308, determining that position using the position sensor 306, and virtual placing the virtual fiducial within the preoperative model at that determined position. The physician can then navigate the first medical instrument 304 to the next position at which it is desired to place a virtual fiducial 308 and repeat the process until all desired virtual fiducials 308 are placed.

In some embodiments, with the preoperative model registered to the patient's anatomy and the output of the position sensor 306, positions for placement of the virtual fiducials 308 can be selected with reference to the preoperative model. For example, in some embodiments, the positions for the virtual fiducials 308 can be determined with reference to the position sensor 306 but at positions that are distanced from the position sensor 306. That is, in some embodiments, the locations of the virtual fiducials 308 need not be coincident with the position sensor 306 (or any other portion of the medical instrument 314). For example, the preoperative model can be displayed to the physician, and the physician can select the placement locations for the virtual fiducials 308 on the displayed preoperative model.

In some embodiments, the positions of the virtual fiducials 308 can be determined preoperatively with reference to the preoperative model. The first medical instrument 304 can then be navigated into the lung 302 to register the preoperative model to the anatomy. In some embodiments, the first medical instrument 304 can be used to verify the placement of the preoperatively selected positions of the virtual fiducials 308, by for example, navigating to locations that correspond to the positions of the virtual fiducials 308. In some embodiments, the physician may then adjust the placement positions of the virtual fiducials 308 intraoperatively, if desired.

In another example, the positions of the virtual fiducials 308 can be determined with reference to intraoperative medical imaging, such as fluoroscopic images. For example, an operator can select the positions of the virtual fiducials 308 on a fluoroscopic image.

The positions of the virtual fiducials 308 may be displayed to the user, for example, on a graphical user interface as shown in FIG. 24.

As shown in FIG. 25B, the positions of the virtual fiducials 308 can be used to define a boundary 309. The boundary 309 may define the resection volume. In some embodiments, the system is configured to fit a line or surface through the virtual fiducials 308 to define the boundary 309. In some embodiments, the boundary 309 may be displayed to the user, for example, on a graphical user interface as shown in FIG. 24. In some embodiments, the boundary 309 is omitted, and the virtual fiducials 308 are used as the boundary.

The boundary 309 (or the virtual fiducials 308 themselves) can be used to guide one or more second medical instruments 314 during resection. Resection can be performed percutaneously, although this need not be the case in all embodiments. In the illustrated embodiments, two second medical instruments 314 are illustrated. The second medical instruments can be, for example, laparoscopic medical instruments, such as those described above with reference to FIGS. 1-20. In some embodiments, the second medical instruments 314 can be positioned on instrument positioning devices, such as a robotic arms. The instrument positioning devices can be robotically controlled. In some embodiments, robotic control can limit or prevent the second medical instruments 314 from breaking or crossing the boundary 309. This can limit or prevent resection of unintended tissue.

In some embodiments, the second medical instruments 314 can be manually controlled. The system can provide an indication of when the second medical instruments 314 are approaching the boundary 309 so that the physician is alerted. The indication can be a visual, audible, or haptic signal.

In some embodiments, during resection with the second medical instruments 314, the first medical instrument 304 remains in the treatment region (e.g., in the lung 302). As described above, the output signal of the position sensor 306 can be used to track patient motion, such as respiration, during the procedure. This motion can be tracked using the position sensor 306. This patient motion can then be compensated for during resection.

Figure 26:
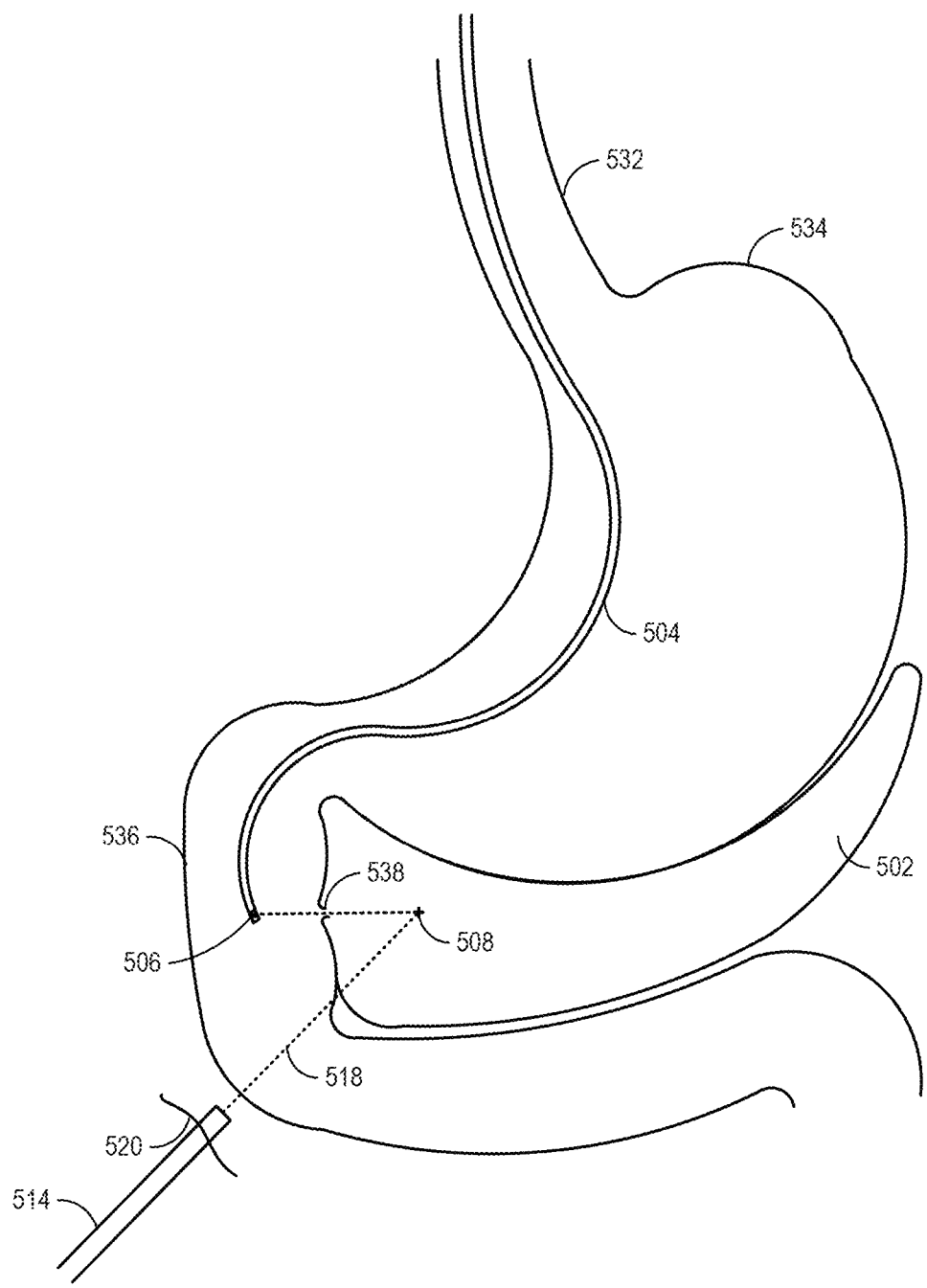
FIG. 26 illustrates an example embodiment of a concomitant endoscopic and percutaneous medical procedure in a gastrointestinal tract.

FIG. 26 illustrates an example embodiment of an endoscopically-assisted percutaneous medical procedure in a gastrointestinal tract. In the illustrated example, a physician desires to take a biopsy the pancreas percutaneously. However, it is generally difficult to ensure that a percutaneously inserted medical instrument will intersect the pancreas. In this example, a percutaneously inserted instrument can be aligned with a target location that is determined based in part on a position sensor of an endoscopically inserted instrument.

In the illustrated example, a first medical instrument 504 is guided through the patient's mouth, esophagus 532, stomach 534, and duodenum 536 to the papilla 538. The papilla 538 can be identified visually, for example, using an optical system on the first medical instrument 504. The first medical instrument 504 includes a position sensor 506 as described above. A target location 508 in the pancreas can be determined relative to the position determined by the position sensor 506. This can be done because the physician knows that the pancreas is located opposite the papilla 538. Thus, the target location 508 can be determined at a position that is distanced from the position sensor 506. The target location 508 can then used as a beacon for aligning and guiding percutaneous insertion of a second medical instrument 514 as described above. For example, an axis 518 of the second medical instrument can be aligned with the target location 508, and then the second medical instrument can be percutaneously inserted through an opening 520 so as to intersect with the target location 508 and take the biopsy. As before, alignment of second medical instrument 514 can be robotically maintained.

FIG. 27A is a flow chart illustrating an embodiment of a method 600 for performing a medical procedure that includes rendezvousing a medical instrument with a target location. The method 600 begins at block 602, at which a first medical instrument is inserted into a treatment region. The treatment region can comprise, for example, a kidney, a bladder, a lung, a stomach, a gastrointestinal tract, etc. The first medical instrument can be an endoscope. In some embodiments, the first medical instrument is inserted into the treatment region through a natural patient orifice. The first medical instrument can be a laparoscope. In some embodiments, the first medical instrument is inserted into the treatment region percutaneously or through a percutaneous opening. The first medical instrument can be robotically controlled, for example, using the robotically-enabled medical systems described above with reference to FIGS. 1-20. The first medical instrument can be manually controlled.

Next, the method 600 moves to block 604, at which a first position of the first medical instrument is determined using a first position sensor on the first medical instrument. The first medical instrument can include a first position sensor. The first position sensor can be an EM sensor, shape sensing fiber, or any other type of sensor for determining position. In some embodiments, the output of the first position sensor can be registered to a preoperative model, such that the position of the first position sensor is determined with reference to the preoperative model. The preoperative model can be developed, for example, based on a CT scan or other methods as described above.

The method 600 then moves to block 606, at which a target location that is distanced from the first position is determined within the treatment region. The target location can represent a rendezvous point for a second medical instrument. The target location can be displayed to the user. In some embodiments, defining the target location within the treatment region comprises determining the target location with reference to the preoperative model. For example, determining the target location with reference to the preoperative model can be accomplished by displaying the preoperative model to a user, and receiving a selection of the target location with reference to the preoperative model.

In some embodiments, a distance and direction between the first position, as determined by the first position sensor, and the target location can be determined. The distance and direction can be calculated, for example, from the registered preoperative model.

In some embodiments, defining the target location within the treatment region can include capturing one or more intraoperative medical images of the treatment region, and defining the target location with reference to the one or more intraoperative medical images. the intraoperative medical images can be one or more fluoroscopic images. The one or more medical images can be registered to the output of the position sensor.

Finally, the method moves to block 608, at which a second medical instrument is guided toward the target location. The second medical instrument can be a laparoscope. In some embodiments, the second medical instrument is inserted into the treatment region percutaneously or through a percutaneous opening. The second medical instrument can be an endoscope. In some embodiments, the second medical instrument is inserted into the treatment region through a natural patient orifice. The second medical instrument can be robotically controlled, for example, using the robotically-enabled medical systems described above with reference to FIGS. 1-20. The second medical instrument can be manually controlled. In some embodiments, initial access is gained by percutaneously inserting the first medical instrument, which can include a position sensor built in. The first medical instrument can be a needle that includes a thin walled sleeve that is left behind in order to create a small access channel into the patient. A second medical instrument, such as a guidewire can then inserted through the sleeve and into the patient, at which point through the sleeve can be removed while ensuring the wire stays in place. Then, the wire can used as a rail for delivering a dilation tool and eventually a larger port.

In some embodiment, guiding the second medical instrument toward the target location can include aligning a second axis of the second medical instrument with the target location, and advancing the second medical instrument toward the target location. In some embodiments, the second medical instrument is attached to a robotic arm, or other instrument positioning device. The robotic arm can restrict motion of the second medical instrument to motion along or around the second axis to maintain alignment with the target location. The robotic arm may provide haptic boundaries that maintain alignment of the second medical instrument.

In some embodiments, the method 600 further comprises determining patient movement with the first position sensor of the first medical instrument. For example, during a procedure, the first medical instrument can remain in the treatment region and the first position sensor can monitor patient movement. In some embodiment, guidance of the second instrument can compensate for the measured patient movement. Patient movement that can be compensated for can include, for example, movement due to respiration.

FIG. 27B is a flow chart illustrating an embodiment of a method 610 for performing a medical procedures that includes placing virtual fiducials to define a boundary. The boundary can be, for example, a resection boundary. The method 610 begins at block 612, at which at which a first medical instrument is inserted into a treatment region. The treatment region can comprise, for example, a kidney, a bladder, a lung, a stomach, a gastrointestinal tract, etc. The first medical instrument can be an endoscope. In some embodiments, the first medical instrument is inserted into the treatment region through a natural patient orifice. The first medical instrument can be a laparoscope. In some embodiments, the first medical instrument is inserted into the treatment region percutaneously or through a percutaneous opening. The first medical instrument can be robotically controlled, for example, using the robotically-enabled medical systems described above with reference to FIGS. 1-20. The first medical instrument can be manually controlled.

Next, the method 610 moves to block 614, at which the first position sensor is registered to a preoperative model. The first medical instrument can include a first position sensor. The first position sensor can be an EM sensor, shape sensing fiber, or any other type of sensor for determining position. In some embodiments, the output of the first position sensor can be registered to a preoperative model, such that the position of the first position sensor is determined with reference to the preoperative model. The preoperative model can be developed, for example, based on a CT scan or other methods as described above.

The method 610 then moves to block 616, at which positions for one or more virtual fiducials are defined to create a boundary with reference to the preoperative model. In some embodiments, determining the positions for the one or more virtual fiducials includes navigating the first medical instrument to a location within the treatment region at which a virtual fiducial will be placed, and defining the location as the position of a virtual fiducial based on the registered output of the first position sensor. In some embodiments, determining the positions for the one or more virtual fiducials includes receiving a user selection of a location at which to place one of the one more virtual fiducials, and determining a virtual fiducial position corresponding to the location with reference to at least a first position determined based on the first position sensor, wherein the virtual fiducial position is distanced from the first position. In some embodiments, a virtual curve or surface is fit to the virtual fiducials to define the boundary. The boundary and/or virtual fiducials can be displayed to the physician.

Next, the method 610 moves to block 618, at which the first medical instrument is positioned away from the boundary. In some embodiments, in this position, patient movement during the procedure can be monitored with the first position sensor of the first medical instrument, as described above. In some embodiments, block 618 can be omitted, and the first medical instrument can remain at the boundary during the procedure. Whether the first instrument remains at the boundary can depend, for example, on the usage of the boundary and timing. For instance, in FIG. 25, the boundary is representative of a region to be removed. In this case, the first instrument can be positioned inside the boundary when the surgeon is resecting the distal part of the lung to provide a better visualization. However, when the surgeon needs to resect the region where the first instrument is located within the boundary, the first instrument should be pulled away to give space for the operation.

Finally, the method 600 moves to block 620, at which a second medical instrument is guided within the treatment region based on the one or more virtual fiducials. The second medical instrument can be a laparoscope. In some embodiments, the second medical instrument is inserted into the treatment region percutaneously or through a percutaneous opening. The second medical instrument can be an endoscope. In some embodiments, the second medical instrument is inserted into the treatment region through a natural patient orifice. The second medical instrument can be robotically controlled, for example, using the robotically-enabled medical systems described above with reference to FIGS. 1-20. The second medical instrument can be manually controlled. In some embodiments, movement of the second medical instrument is limited or restricted such that the second medical instrument cannot be moved beyond the boundary. In some embodiments, limits or restrictions on movements of the second medical instrument are created using haptic boundaries when the second medical instrument is attached to a robotic arm or other instrument positioning device.

In some embodiments, the methods 600, 610 can be performed, for example, using the robotically-enabled medical systems described above with reference to FIGS. 1-20.

The concomitant endoscopic and percutaneous (e.g., laparoscopic) systems and methods described above can provide numerous advantages, including providing improved placement precision for endoscopic or laparoscopic tools and providing well defined or otherwise improved resection boundaries.

The concomitant endoscopic and percutaneous (e.g., laparoscopic) systems and methods described above can also be used during combined endoscopic and laparoscopic surgery (CELS), which can be performed robotically using the systems described above. An example of a procedures that can be advantageously performed using CELS is colonic polyp resection, although other examples also exist. Polyps can be evaluated as to whether they can be removed endoscopically based on their size, type, and location. When polyps cannot be removed endoscopically, they can be removed via segmental colectomy, which is accompanied with a comparatively high complication rate and increased recovery time. During poly resection, CELS can enable extraluminal mobilization of the colon (with laparoscopic instruments) to make the polyp easier to resect intraluminally (with endoscopic instruments).

When performed manually, CELS typically requires at least two physicians (to control the laparoscopic and endoscopic instruments respectively) and two assistants (to hold the laparoscope and colonoscope respectively). While one physician is moving an instrument, the remaining providers may hold their instruments still, which may be physically demanding over extended periods of time. There may be additional staff members in the room to assist with instrument exchange, pass suture or gauze, handle specimens after removal, and control laparoscopic instruments, etc. Further, communication between the two operating physicians can be slow and difficult. For example, it may be difficult to for one physician to communicate the location of the instrument that he or she is controlling to the other physician or vice versa. The systems and methods described above may reduce or eliminate these difficulties that can occur when CELS is performed manually by allowing a single physician to control both instruments and/or providing improved rendezvous between the two instruments.

In addition to the above example of endoscopic diagnosis and surgical resection of a cancerous tumor, other example medical procedures may benefit from the systems and methods described herein, including bronchoscopic localization of lung cancer with simultaneous thoracoscopic resection, endoscopic localization of gastrointestinal cancer with laparoscopic resection, endoscopic localization and resection of gastrointestinal cancer with laparoscopic assistance, endoscopic imaging or visualization for gastrointestinal reconstructive procedures, such as gastrectomy, roux-en-y-gastric bypass, etc., ureteroscopic stone/tumor localization and percutaneous removal/resection. In some embodiments, such procedures can be performed in a single treatment episode. In some embodiments, such procedures can be performed with a minimal number of clinicians, and in some cases, a single physician. Furthermore, in some embodiments, simultaneous procedures can be performed using a single type of console to control the simultaneous procedures.

In some instances, one instrument (e.g., an endoscopically inserted instrument) may be able to provide better visualization of a treatment site (e.g., a lesion) while another instrument (e.g., a laparoscopically inserted instrument) may be better suited to treat (e.g., biopsy or resect) the treatment site. The reverse may also be true. In some cases, the laparoscopically inserted instrument can provide better visualization, while the endoscopically inserted instrument can provide better treatment. The methods and systems described above can advantageously allow each instrument to be used in the manner that is better suited for, while relaying information that can be used to guide the other instrument. This can advantageously allow greater precision and reduce total time for the procedure, providing improved patient outcomes.

3. Implementing Systems and Terminology.

Implementations disclosed herein provide systems, methods and apparatus for endoscopically-assisted percutaneous medical procedures.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system comprising:
   an endoscope configured to be inserted into a treatment region of a patient through a natural orifice of the patient, the endoscope comprising an elongated shaft and an electromagnetic (EM) sensor disposed at a distal end portion of the elongated shaft;
   a first robotic arm configured to couple to and control movement of the endoscope;
   a needle configured to be inserted into the treatment region percutaneously, the needle including a position sensor;
   at least one computer-readable memory having stored thereon executable instructions; and
   one or more processors in communication with the at least one computer-readable memory and configured to execute the executable instructions to cause the system to at least:
      determine a first position of the endoscope within the treatment region based on an output of the EM sensor;
      determine a target location from the determined first position;
      determine, based on the target location, a target zone for positioning the needle on the patient's skin;
      determine whether a distal end of the needle is within the target zone;
      provide an indication of whether the distal end of the needle is within the target zone;
      determine a target trajectory for reaching the target location, the target trajectory representing a line that passes through the target location;
      determine an orientation of an axis of the needle based on an output of the position sensor; and
      cause an alignment interface to be displayed that includes an outer boundary, a target indicator representing the target location and positioned in a center of the outer boundary, and an instrument indicator, a distance of the instrument indicator to the target indicator indicating an amount of alignment of the axis of the needle to the target trajectory, the target indicator being configured to remain in the center of the outer boundary and the instrument indicator being configured to move around within the outer boundary as the amount of alignment changes.

2. The system of claim 1, wherein the executable instructions further cause the system to register an output of the EM sensor with a coordinate frame of a preoperative model, and wherein determining the first position of the endoscope within the treatment region comprises determining the first position with reference to the preoperative model.

3. The system of claim 2, wherein determining the target location comprises determining the target location with reference to the preoperative model.

4. The system of claim 3, wherein determining the target location with reference to the preoperative model comprises:
   displaying the preoperative model to a user; and
   receiving user input corresponding to the target location with reference to the preoperative model.

5. The system of claim 4, wherein determining the target location comprises determining, with reference to the preoperative model, a difference between the determined first position and the target location.

6. The system of claim 1, further comprising a display configured to display the alignment interface.

7. The system of claim 1, wherein determining the target location comprises:
   capturing one or more intraoperative medical images of the treatment region; and
   defining the target location with reference to the one or more intraoperative medical images.

8. The system of claim 7, wherein the one or more intraoperative medical images comprise one or more fluoroscopic images.

9. The system of claim 7, wherein the executable instructions further cause the system to register the output of the EM sensor to the one or more intraoperative medical images.

10. The system of claim 1, further comprising a second robotic arm, wherein the needle is attached to the second robotic arm, and the second robotic arm is configured to restrict motion of the needle to motion along the axis of the needle.

11. The system of claim 1, wherein the alignment interface provides an axial perspective view with respect to the axis of the needle.

12. The system of claim 1, wherein the alignment interface provides a view from a perspective of the axis of the needle.

13. A method for performing a medical procedure, the method comprising:
   inserting an endoscope into a treatment region of a patient through a natural orifice of the patient, the endoscope comprising an elongated shaft and an electromagnetic (EM) sensor disposed at a distal end portion of the elongated shaft;

determining a first position of the endoscope within the treatment region with the EM sensor;

determining, based at least in part on the determined first position of the endoscope, a target zone for positioning a needle on the patient's skin;

determining whether a distal end of the needle is within the target zone;

providing an indication of whether the distal end of the needle is within the target zone;

determining a target trajectory based at least in part on the determined first position of the endoscope;

determining an orientation of an axis of the needle based at least in part on an output of a position sensor on the needle; and displaying an alignment interface that includes an outer boundary, a target indicator representing the target trajectory and positioned in a center of the outer boundary, and an instrument indicator, a distance of the instrument indicator to the target indicator indicating an amount of alignment of the axis of the needle to the target trajectory, the target indicator being configured to remain in the center of the outer boundary and the instrument indicator being configured to move around within the outer boundary as the amount of alignment changes.

14. The method of claim 13, further comprising registering the output of the EM sensor with a coordinate frame of a preoperative model, and wherein determining the first position of the endoscope within the treatment region comprises determining the first position with reference to the preoperative model.

15. The method of claim 14, further comprising:
displaying the preoperative model to a user; and
receiving a selection of a target location with reference to the preoperative model.

16. The method of claim 15, further comprising:
determining, with reference to the preoperative model, a difference between the determined first position and the target location.

17. The method of claim 13, wherein:
the needle is attached to a robotic arm; and
the robotic arm restricts motion of the needle to motion along the axis of the needle.

18. A system comprising:
an endoscope configured to be inserted into a treatment region of a patient through a natural orifice of the patient, the endoscope comprising an elongated shaft and an electromagnetic (EM) sensor disposed at a distal end portion of the elongated shaft;

a first robotic arm configured to couple to and control movement of the endoscope;

a needle configured to be inserted into the treatment region percutaneously, the needle including a position sensor;

at least one computer-readable memory having stored thereon executable instructions; and one or more processors in communication with the at least one computer-readable memory and configured to execute the executable instructions to cause the system to at least:
determine a first position of the endoscope within the treatment region based on an output of the EM sensor;
determine a target location from the determined first position;
determine a target trajectory for reaching the target location, the target trajectory representing a line that passes through the target location;
determine a target region associated reaching the target location, the target region including a cone-shaped boundary around the target trajectory;
determine an orientation of an axis of the needle based on an output of the position sensor;
determine an amount of alignment of the needle to the target trajectory based on the target region and the orientation of the axis of the needle; and
cause an alignment interface to be displayed that includes an outer boundary, a target indicator representing the target location and positioned in a center of the outer boundary, and an instrument indicator, a distance of the instrument indicator to the target indicator indicating the amount of alignment of the needle to the target trajectory, the target indicator being configured to remain in the center of the outer boundary and the instrument indicator being configured to move around within the outer boundary as the amount of alignment changes.

19. The system of claim 18, wherein the executable instructions further cause the system to register an output of the EM sensor with a coordinate frame of a preoperative model, and wherein determining the first position of the endoscope within the treatment region comprises determining the first position with reference to the preoperative model.

20. The system of claim 19, wherein determining the target location comprises determining the target location with reference to the preoperative model.

21. The system of claim 20, wherein determining the target location with reference to the preoperative model comprises:
displaying the preoperative model to a user; and
receiving user input corresponding to the target location.

22. The system of claim 19, wherein determining the target location comprises determining, with reference to the preoperative model, a difference between the determined first position and the target location.

23. The system of claim 18, further comprising a display configured to display the alignment interface.

24. The system of claim 18, wherein determining the target location comprises:
capturing one or more intraoperative medical images of the treatment region; and
defining the target location with reference to the one or more intraoperative medical images.

25. The system of claim 24, wherein the one or more intraoperative medical images comprise one or more fluoroscopic images.

* * * * *